US006893846B2

(12) United States Patent
Hanson et al.

(10) Patent No.: US 6,893,846 B2
(45) Date of Patent: May 17, 2005

(54) PRIMERS FOR USE IN DETECTING BETA-LACTAMASES

(75) Inventors: Nancy D. Hanson, Grentna, NE (US); Christine C. Sanders, Englewood, FL (US); Anton F. Ehrhardt, Omaha, NE (US)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 09/814,252

(22) Filed: Mar. 21, 2001

(65) Prior Publication Data

US 2005/0064398 A1 Mar. 24, 2005

Related U.S. Application Data

(62) Division of application No. 09/407,818, filed on Sep. 28, 1999, now Pat. No. 6,242,223.
(60) Provisional application No. 60/121,765, filed on Feb. 26, 1999, and provisional application No. 60/102,181, filed on Sep. 28, 1998.

(51) Int. Cl.$^7$ .......................... C12P 19/34; C12Q 1/68; C07H 21/02; C07H 21/04; C07H 21/00
(52) U.S. Cl. ...................... 435/91.2; 435/6; 435/91.1; 536/23.1; 536/24.3; 536/24.33; 536/25.3
(58) Field of Search ........................... 435/6, 91.1, 183; 436/94; 536/23.1, 24.3, 24.33, 25.3

(56) References Cited

U.S. PATENT DOCUMENTS

| 4,683,194 A | 7/1987 | Saiki et al. |
|---|---|---|
| 4,683,195 A | 7/1987 | Mullis et al. |
| 5,994,066 A | 11/1999 | Bergeron et al. |
| 6,001,564 A | 12/1999 | Bergeron et al. |
| 6,242,223 B1 | 6/2001 | Hanson et al. |

FOREIGN PATENT DOCUMENTS

WO   WO 91/08305   *  6/1991

OTHER PUBLICATIONS

Arlet al., Construction by polymerase chain reaction and intragenic DNA probes for three main types of transferable beta–lactamases (TEM, SHV, CARB). FEMS Microbiology Letter, 82, 19–26, 1991.*

Alksne et al., "Expression of the AsbA1, OXA–12, and AsbM1 β–Lactamases in *Aeromonas jandaei* AER 14 IS Coordinated by a Two–Component Regulon," *Journal of Bacteriology*, 179(6):2006–2013 (1997).*

Daniel et al., "OXA–15, an Extended–Spectrum Variant of OXA–2 β–Lactamase, Isolated from a *Pseudomonas aeruginosa* Strain," *Antimicrobial Agents and Chemotherapy*, 41(4):785–790 (1997).*

Rasmussen et al., "Cloning and Expression of a Cloxacillin–Hydrolyzing Enzyme and a Cephalosporinase from *Aeromonas sobria* AER 14M in *Escherichia coli*: Requirement for an *E. coli* Chromosomal Mutation for Efficient Expression of the Class D Enzyme," *Antimicrobial Agents and Chemotherapy*, 38(9):2078–2085 (1994).*

Scoulica et al., "Molecular Characterization of the OXA–7 β–Lactamase Gene," *Antimicrobial Agents and Chemotherapy*, 39(6):1379–1382 (1995).*

Tolmasky et al., "Genetic Organization Antibiotic Resistant Genes (aac(6')–Ib, aadA. and OXA–9) in the Multiresistance Transposon TnI33I," *Plasmid*, 29:31–40 (1993).*

Acar et al., "Nature of the Resistance Problem," *Clin. Inf. Dis.*, 24(Suppl 1):S1 (1997).

Arlet et al., "Construction by polymerase chain reaction and intragenic DNA probes for three main types of transferable β–lactamases (TEM, SHV, CARB)," *FEMS Microbiol. Lett.*, 82:19–25 (1991).

Arlet et al., "Molecular characterization by PCR–restriction fragment length polymorphism of TEM β–lactamases," *FEMS Microbiol Lett.*, 134:203–208 (1995).

Arlet et al., "Substitution of alanine for aspartate at position 179 in the SHV–6 extended–spectrum β–lactamase," *FEMS Microbiol Lett.*, 152:163–167 (1997).

Barnaud et al., "Cloning and sequencing of the gene encoding the AmpC β–lactamase of *Morganella morganii*," *FEMS Microbiol Lett.*, 148:15–20 (1997).

Bauernfeind et al., "A New Plasmidic Cefotaximase in a Clinical Isolate of *Escherichia coli*," *Infection*, 18(5):294–298 (1990).

Billot–Klein et al., "Nucleotide Sequence of the SHV–5 β–Lactamase Gene of a *Klebsiella pneumonia* Plasmid," *Antimicrob. Agents Chemother.*, 34(12):2439–2441 (1990).

Birnboim et al., "A rapid alkaline extraction procedure for screening recombinant plasmid DNA," *Nucleic Acids Res.*, 7(6):1513–1523 (1979).

Bradford et al., "SHV–7, a Novel Cefotaxime–Hydrolyzing β–Lactamase, Identified in *Escherichia coli* Isolates from Hospitalized Nursing Home Patients," *Antimicrob. Agents Chemother.*, 39(4):899–905 (1995).

Bradford et al., "Multiply Resistant *Klebsiella pneumoniae* Strains from Two Chicago Hospitals: Identification of the Extended–Spectrum TEM–12 and TEM–10 Ceftazidime–Hydrolyzing β–Lactamases in a Single Isolate," *Antimicrob. Agents Chemother.*, 38(4): 761–766 (1994).

Bret et al., "Chromosomally Encoded AmpC–Type β–Lactamase in a Clinical Isolate of *Proteus mirabilis*," *Antimicrob. Agents Chemother.*, 42(5):1110–1114 (1998).

(Continued)

Primary Examiner—Kenneth R. Horlick
Assistant Examiner—Frank Lu
(74) *Attorney, Agent, or Firm*—Mueting, Raasch & Gebhardt, P.A.

(57) ABSTRACT

Oliognucleotide primers are provided that are specific for nucleic acid characteristic of certain beta-lactamases. The primers can be employed in methods to identify nucleic acid characteristic of family-specific beta-lactamase enzymes in samples, and particularly, in clinical isolates of Gram-negative bacteria.

3 Claims, No Drawings

OTHER PUBLICATIONS

Brun–Buisson et al., "Transferable Enzymatic Resistance to Third–Generation Cephalosporins During Nosocomial Outbreak of Multiresistant Klebsiella Pneumoniae," *The Lancet,* 2:302–306 (1987).

Burns et al., "An Integrated Nanoliter DNA Analysis Device," *Science,* 282:484–487 (1998).

Canica et al., "Molecular Diversity and Evolution of bla$_{tem}$ Genes Encoding β–Lactamases Resistant to Clavulanic Acid in Clinical *E. coli,*" *J. Mol. Evol.,* 44:57–65 (1997).

Carter et al., "Use of a non–radioactive hybridisation assay for direct detection of gram–negative bacteria carrying TEM β–lactamase genes in infected urine," *J. Med. Microbiol,* 28:113–117 (1989).

Check, "Clinical Microbiology Eyes Nucleic Acid–Based Technologies," *ASM News,* 64(2):84–89 (1998).

Crea et al., "Chemical synthesis of genes for human insulin," *Proc. Natl. Acad. Sci. USA,* 75(12):5765–5769 (1978).

Crosa et al., "Plasmids," *Manual of Methods for General Bacteriology,* Gerhardt et al., eds., American Society for Microbiology, Washington, DC, Ch. 15, pp. 266–282 (1981).

Curran et al., "A rapid immunoassay method for the direct detection of PCR products: application to detection of TEM β–lactamase genes," *J. Med. Microbiol.,* 45:76–78 (1996).

Galleni et al., "Sequence and comparative analysis of three *Enterobacter cloacae* ampC β–lactamase genes and their products," *Biochem. J.,* 250, 753–760 (1988).

Gold et al., "Antimicrobial–Drug Resistance," *The New England Journal of Medicine,* 335(19):1445–1453 (1996).

Gonzalez Leiza et al., "Gene sequence and biochemical characterization of FOX–1 from *Klebsiella pneumoniae,* a new AmpC–type plasmid–mediated beta–lactamase with two molecular variants," *Antimicrob. Agents Chemother.,* 38(9):2150–7 (1994).

Hanson et al., "Molecular Characterization of a Multiply Resistant *Klebsiella pneumoniae,*" Abstract C–59, *37$^{th}$ ICAAC,* Toronto, Ontario, Canada, Sep. 28–Oct. 1 (1997).

Hanson et al., "A Novel TEM–Type Extended Spectrum Beta–Lactamase Expressed in Three Different Genera of Enterobacteriaceae from South Africa," Abstract C–5, p. 70, *38$^{th}$ ICAAC,* San Diego, California, Sep. 24–27 (1998).

Hanson et al., "Molecular characterization of a multiply resistant *Klebsiella pneumoniae* encoding ESBLs and a plasmid–mediated AmpC," *J. Antimicrob. Chemother.,* 44:377–380 (1999).

Hanson et al., "Regulation of Inducible AmpC Beta–Lactamase Expression Among Enterobacteriaceae," *Curr. Pharmac. Design,* 5(11):881–894 (1999).

Hibbert–Rogers et al., "Convergent evolution of TEM–26, a β–lactamase with extended–spectrum activity," *J. Antimicrob. Chemother.,* 33:707–720 (1994).

Huletsky et al., "Nucleotide Sequence and Phylogeny of SHV–2 β–Lactamase," *Antimicrob. Agents Chemother.,* 34(9):1725–1732 (1990).

Jacoby et al., "More Extended–Spectrum β–Lactamases," *Antimicrob. Agents Chemother.,* 35(9):1697–1704 (1991).

Jarlier et al., "Extended Broad–Spectrum β–Lactamases Conferring Transferable Resistance to Newer β–Lactam Agents in Enterobacteriaceae: Hospital Prevalence and Susceptibility Patterns," *Rev. Infect. Dis.,* 10(4):867–878 (1988).

Jones, "The Emergent Needs for Basic Research, Education, and Surveillance of Antimicrobial Resistance: Problems Facing the Report from the American Society for Microbiology Task Force on Antibiotic Resistance," *Diagn. Microbiol. Infect. Disease,* 25:153–161 (1996).

Jones, "Important and Emerging β–Lactamase–mediated Resistances in Hospital based Pathogens: The Amp C Enyzymes," *Diagn. Microbiol. Infect. Dis.,* 31:461 466 (1998).

Leung et al., "Rarity of transferable β–lactamase production by Klebsiella species," *J. Antimicrob. Chemother.,* 39:737–745 (1997).

M'Zali et al., "Brief reports: Detection of mutations conferring extended–spectrum activity on SHV β–lactamases using polymerase chain reaction single strand conformational polymorphism (PCR–SSCP)," *J. Antimicrob. Chemother.,* 37:797–802 (1996).

Mabilat et al., "Direct Sequencing of the Amplified Structural Gene and Promoter for the Extended–Broad–Spectrum β–Lactamase TEM–9 (RHH–1) of *Klebsiella pneumoniae,*" *Plasmid,* 23:27–34 (1990).

Mabilat et al., "Development of "Oligotyping" for Characterization and Molecular Epidemiology of TEM β–Lactamase in Members of the Family Enterobacteriaceae," *Antimicrob. Agents Chemother.,* 34(11):2210–2216 (1990).

Maniatis et al., *Molecular Cloning: A Laboratory Manual,* Cold Spring Harbor, NY (Title page, Publication page, and Table of Cotnents only) 8 pgs. (1982).

Marchese et al., "Characterization of FOX–3, an AmpC–Type Plasmid–Mediated β–Lactamase from an Italian Isolate of *Klebsiella oxytoca,*" *Antimicrob. Agents Chemother.,* 42(2):464–467 (1998).

Martineau, Species–specific and ubiquitous DNA–based assays for rapid identification of Staphylococcus epidermidis, *J Clin Microbiol.,* 34(12):2888–93 (1996).

Medeiros, "Recent Increases in Resistance: Mechanisms and Organisms: Evolution and Dissemination of β–Lactamases Accelerated by Generations of β–Lactam Antibiotics," *Clin. Inf. Dis.,* 24(Suppl 1):S19–45 (1997).

Mercier et al., "Cloning of SHV–2, OHIO–1, and OXA–6 β–Lactamases and Cloning and Sequencing of SHV–1 β–Lactamase," *Antimicrob. Agents Chemother.,* 34(8):1577–1583 (1990).

Mugnier et al., "A TEM–Derived Extended–Spectrum β–Lactamase in *Pseudomonas aeruginosa,*" *Antimicrob. Agents Chemother.,* 40(11):2488–2493 (1996).

Mullis et al., "Specific Enzymatic Amplification of DNA In Vitro: The Polymerase Chain Reaction," *Cold Spring Harbor Symposia on Quantitative Biology,* Cold Spring Harbor Laboratory, Cold Spring Harbor, NY, 51:263–273 (1986).

Mullis et al., "Specific Enzymatic Amplification of DNA In Vitro; The Polymerase Chain Reaction," *Milestones in Biotechnology: Classic Papers on Genetic Engineering,* Davies et al., eds., Buterworth–Heinemann, Stoncham, MA, pp. 17–27 (1992).

Naumovski et al., "Outbreak of Ceftazidime Resistance Due to a Novel Extended–Spectrum β–Lactamase in Isolates from Cancer Patients," *Antimicrob. Agents Chemother.,* 36(9):1991–1996 (1992).

Nordmann et al., "Characterization of a Novel Extended–Spectrum β–Lactamase from *Pseudomonas aeruginosa,*" *Antimicrob. Agents Chemother.,* 37(5): 962–969 (1993).

Nüesch–Inderbinen et al., "Detection of Genes Coding for Extended–Spectrum SHV Beta–Lactamases in Clinical Isolates by a Molecular Genetic Method, and Comparison with the E Test," *Eur. J. Clin. Microbiol. Infect. Dis.*, 15:398–402 (1996).

O'Callaghan et al., "Inhibition of β–Lactamase Decomposition of Cephaloridine and Cephalothin by Other Cephalosporins," *Antimicrob. Agents Chemother.*, 337–343 (1967).

Philippon et al., "Minireview—Extended–Spectrum β–Lactamases," *Antimicrob. Agents Chemother.*, 33(8):1131–1136 (1989).

Piddock et al., "Prevalence and mechanism of resistance to 'third–generation' cephalosporins in clinically relevant isolates of Enterobacteriaceae from 43 hospitals in the UK, 1990–1991," *J. Antimicrob. Chemother.*, 39:177–187 (1997).

Pitout et al., "β–Lactamases Responsible for Resistance to Expanded–Spectrum Cephalosporins among *Klebsiella pneumoniae, Escherichia coli* and *Proteus mirabilis* Isolates Recovered in South Africa," 96th ASM General Meeting, Poster and Abstract A–46, p. 141 (May 1996).

Pitout et al., "β–Lactamases Responsible for Resitance to Expanded–Spectrum Cephalosporins in *Klebsiella pneumoniae, Escherichia coli,* and *Proteus mirabilis* Isolates Recovered in South Africa," *Antimicrob. Agents Chemother.*, 42(6):1350–1354 (1998).

Pitout et al., "Plasmid–Mediated Resistance to Expanded––Spectrum Cephalosporins among *Enterobacter aerogenes* Strains," *Antimicrob. Agents Chemother.*, 42(3):596–600 (1998).

Prodinger et al., "Molecular Epidemiology of *Klebsiella pneumoniae* Producing SHV–5 β–Lactamase: Parallel Outbreaks Due to Multiple Plasmid Transfer," *J. Clin. Microbio.*, 34(3):564–568 (1996).

Resigner PCR from Research Genetics. Advertisement in *Mucleic Acid Res.*, 22(15).

Saiki et al., "Enzymatic Amplification of β–Globin Genomic Sequences and Restriction Site Analysis for Diagnosis of Sickle Cell Anemia," *Science*, 230, 1350–1354 (1985).

Saiki et al., "Analysis of enzymatically amplified β–globin and HLA–DQα DNA with allele–specific oligonucleotide probes," *Nature*, 324:163–166 (1986).

Sanchez et al., "The E–Test Applied to Susceptibility Tests of Gonococci, Multiply–Resistant Enterococci, and Enterobacteriaceae Producing Potent β–Lactamases," *Diagn. Microbiol. Infect. Dis.*, 15:459–463 (1992).

Sanders et al., "New Service Notification," distributed by Center for Research in Anti–Infectives and Biotechnology Creighton University School of Medicine (Sep. 28, 1997).

Sanders et al., "Characterization of β–Lactamases In Situ on Polyacrylamide Gels," *Antimicrob. Agents Chemother.*, 30(6):951–952 (1986).

Sanders, Jr. et al., "Enterobacter spp.: Pathogens Poised to Flourish at the Turn of the Century," *Clin. Microbiol. Rev.*, 10(2):220–241 (1997).

Sayeed et al., "Expression of *Aeromonas caviae bla* genes in *Escherichia coli*," *J. Antimicrob. Chemother.*, 38:435–441 (1996).

Scharf et al., "Direct Cloning and Sequence Analysis of Enzymatically Amplified Genomic Sequences," *Science*, 233, 1076–1078 (1986).

Schmitz et al., "Specific information concerning taxonomy, pathogenicity and methicillin resistance of staphylococci obtained by a multiplex PCR," *J. Med. Microbiol.*, 46:773–778 (1997).

Sirot et al., "A Complex Mutant of TEM–1 β–Lactamase with Mutations Encountered in Both IRT–4 and Extended–Spectrum TEM–15, Produced by an *Escherichia coli* Clinical Isolate," *Antimicrob. Agents Chemother.*, 41(6):1322–1325 (1997).

Sutcliffe, "Nucleotide sequence of the ampicillin resistance gene of *Escherichia coli* plasmid pBR322," *Proc. Natl. Acad. Sci. USA*, 75(8):3737–3741 (1978).

Tenover et al., "Development of PCR Assays to Detect Ampicillin Resistance Genes in Cerebrospinal Fluid Samples Containing *Haemophilus influenzae*," *J. Clin. Microb.*, 32(11):2729–2737 (1994).

Tenover et al., "SHEA Position Paper: How to Select and Interpret Molecular Strain Typing Methods for Epidemiological Studies of Bacterial Infections: A Review for Healthcare Epidemiologists," *Infect. Control and Hosp. Epidemiol.*, 18(6):426–439 (1997).

Thomson et al., "High–Level Resistance to Cefotaxime and Ceftazidime in *Klebsiella pneumoniae* Isolates from Cleveland, Ohio," *Antimicrob. Agents Chemother.*, 35(5):1001–1003 (1991).

Thomson et al., "Detection of Extended–Spectrum β–Lactamases in Members of the Family Enterobacteriaceae Comparison of the Double–Disk and Three–Dimensional Tests," *Antimicrob. Agents Chemother.*, 36(9):1877–1882 (1992).

Tolmasky, "Sequencing and Expression of aadA, bla, and tnpR from the Multiresistance Transposon Tn1331," *Plasmid*, 24, 218–226 (1990).

Towner, "Leading article: Detection of antibiotic resistance genes with DNA probes," *J. Antimicrob. Chemother.*, 30:1–2 (1992).

Vercauteren et al., "Comparison of Screening Methods for Detection of Extended–Spectrum β–Lactamases and Their Prevalence among Blood Isolates of *Escherichia coli* and Klebsiella spp. in a Belgian Teaching Hospital," *J. Clin. Microb.*, 35(9):2191–2197 (1997).

Walsh et al., "Sequence analysis of two chromosomally mediated inducible β–lactamases from *Aeromonas sobria*, strain 163a, one a class D penicillinase, the other an AmpC cephalospoinase," *J. Antimicrob. Chemother.*, 36:41–52 (1995).

Zhou et al., "Emergence of Clinical Isolates of *Escherichia coli* Producing TEM–1 Derivatives or an OXA–1 β–Lactamase Conferring Resistance to β–Lactamase Inhibitors," *Antimicrob. Agents Chemother.*, 38(5):1085–1089 (1994).

Leegaard et al., "Antibiotic resistance mechanisms in Salmonella species causing bacteraemia in Malawi and Kenya", *APMIS*, 104:302–306 (1996).

Siu et al., "Correlation of in vitro susceptibility testing results for amoxicillin–clavulanate and ampicillin–sulbactam using a panel of beta–lactamase–producing Enterobacteriaceae", *APMIS*, 106:917–920 (1998).

Speldooren et al., "Discriminatory detection of inhibitor–resistant beta–lactamases in *Escherichia coli* by single–strand conformation polymophism–PCR", *Antimicrobial Agents and Chemotherapy*, 42:879–884 (1998).

Vahaboglu et al., "Practical approach for detection and identification of OXA–10–derived ceftazidime–hydrolyzing extended spectrum beta–lactamses", *J. Clin. Microbiology*, 36:827–829 (1998).

Sandvang et al., Characterisation of integrons and antibiotic resistance genes in Danish multiresistant Salmonella enterica Typhimurium DT 104. FEMS Microbiology Letters, 157, 177–181, Dec. 1997.*

* cited by examiner

```
                        SEQUENCE LISTING

<160> NUMBER OF SEQ ID NOS: 45

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1
tgcttaatca gtgaggcacc                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
agatcagttg ggtgcacgag                                              20

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 3
cttggtctga cagttacc                                                18

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 4
tgtcgccctt attcc                                                   15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 5
tcggggaaat gtgcg                                                   15

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
atcgtccacc atccactgca                                              20
```

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
gggaaacgga actgaatgag                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
tagtggatct ttcgctccag                                                    20

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 9
gctctgcttt gttattc                                                       17

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 10
cactcaagga tgtattgtg                                                     19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 11
ttagcgttgc cagtgctcg                                                     19

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 12
ggaacagact gggctttcat c                                                  21

<210> SEQ ID NO 13
<211> LENGTH: 15
<212> TYPE: DNA
<213> ORGANISM: Artificial Sequence
<220> FEATURE:
```

<223> OTHER INFORMATION: Description of Artificial Sequence: Primer

<400> SEQUENCE: 13
ggacatcccc ttgac                                                                15

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
gtggattcac ttctgccacg                                                           20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
cttctggcat gccctatgag                                                           20

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 16
catgacccag ttcgccatat cctg                                                      24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 17
attcgtatgc tggatctcgc cacc                                                      24

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 18
ctggcaacca caatggactc cg                                                        22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 19
gccagttcag catctcccag cc                                                        22

```
<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
cgtgaccaac aacgcccagc                                              20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 21
ccagatagcg aatcagatcg c                                            21

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 22
ccagccgatg ctcaaggag                                               19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 23
cacgaacgcc acataggcg                                               19

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 24
ggcattggga tagttgcggt tg                                           22

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 25
ttactacaag gtcggcgaca tgacc                                        25

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Primer
```

```
<400> SEQUENCE: 26
ggatcacact attacatctc gc                                        22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 27
cgtatggttg agtttgagtg gc                                        22

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 28
gcgacctggt taactacaat ccc                                       23

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 29
cggtagtatt gcccttaagc c                                         21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 30
cggaaaagca cgtcgatggg                                           20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 31
gcgatatcgt tggtggtgcc                                           20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 32
ctcgatgatg cgtgcttcgc                                           20

<210> SEQ ID NO 33
<211> LENGTH: 20
```

```
<212> TYPE: DNA
<213> ORGANISM: Artificial Sequence
<220> FEATURE:
<223> OTHER INFORMATION: Description of Artificial Sequence: Primer

<400> SEQUENCE: 33
gcgactgtga tgtataaacg                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 34
cgtcgctcac catatctccc                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 35
cctctcgtgc tttagacccg                                              20

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 36
cgctgggaaa cctattcgg                                               19

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 37
ctgccatcca gtttcttcgg g                                            21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 38
ggtggcattg acaaattctg g                                            21

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 39
```

-continued

```
cccaccatgc gacaccag                                              18

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 40
tgtgcaacgc aaatggcac                                             19

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 41
cgaccccaag tttcctgtaa gtg                                        23

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 42
aggcacgata gttgtggcag ac                                         22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 43
cactcaaccc atcctaccca cc                                         22

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 44
cgaacgaatc attcagcacc g                                          21

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 45
cggcaatgtt ttactgtagc gcc                                        23
```

PRIMERS FOR USE IN DETECTING BETA-LACTAMASES

This application is a divisional, of U.S. Ser. No. 09/407,818, filed Sep. 28, 1999, now U.S. Patent No. 6,242,223, issued 05 Jun. 2001, entitled "Primers for Use in Detecting Beta-Lactamases," which claims the benefit of U.S. patent application Ser. No. 60/102,181, filed Sep. 28, 1998, entitled "Primers for Use in Detecting Beta-Lactamases," and U.S. patent application Ser. No. 60/121,765, filed Feb. 26, 1999, also entitled "Primers for Use in Detecting Beta-Lactamases." All three applications are incorporated herein by reference.

BACKGROUND

A disturbing consequence of the use, and over-use, of beta-lactam antibiotics (e.g., penicillins and cephalosporins) has been the development and spread of beta-lactamases. Beta-lactamases are enzymes that open the beta-lactam ring of penicillins, cephalosporins, and related compounds, to inactivate the antibiotic. The production of beta-lactamases is an important mechanism of resistance to beta-lactam antibiotics among Gram-negative bacteria.

Expanded-spectrum cephalosporins have been specifically designed to resist degradation by the older broad-spectrum beta-lactamases such as TEM-1, 2, and SHV-1. Microbial response to the expanded-spectrum cephalosporins has been the production of mutant forms of the older beta-lactamases called extended-spectrum beta-lactamases (ESBLs). Although ESBL-producing Enterobacteriaceae were first reported in Europe in 1983 and 1984, ESBLs have now been found in organisms of diverse genera recovered from patients in all continents except Antarctica. The occurrence of ESBL-producing organisms varies widely with some types more prevalent in Europe (TEM-3), others more prevalent in the United States (TEM-10, TEM-12 and TEM-26), while others appear worldwide (SHV-2 and SHV-5). These enzymes are capable of hydrolyzing the newer cephalosporins and aztreonam. Studies with biochemical and molecular techniques indicate that many ESBLs are derivatives of older TEM-1, TEM-2, or SHV-1 beta-lactamases, some differing from the parent enzyme by one to four amino acid substitutions.

In addition, resistance in *Klebsiella pneumoniae* and *Escherichia coli* to cephamycins and inhibitor compounds such as clavalante have also arisen via acquisition of plasmids containing the chromosomally derived AmpC beta-lactamase, most commonly encoded by *Enterobacter cloacae, Pseudomonas aeruginosa*, and *Citrobacter freundii*.

It is of particular concern that genes encoding the beta-lactamases are often located on large plasmids that also contain genes for resistance to other antibiotic classes including aminoglycosides, tetracycline, sulfonamides, trimethoprim, and chloramphenicol. Furthermore there is an increasing tendency for pathogens to produce multiple beta-lactamases. These developments, which occur over a wide range of Gram-negative genera, represent a recent evolutionary development in which common Gram-negative pathogens are availing themselves of increasingly complex repertoires of antibiotic resistance mechanisms. Clinically, this increases the difficulty of identifying effective therapies for infected patients.

Thus, there is a need for techniques that can quickly and accurately identify the types of beta-lactamases that may be present in a clinical isolate or sample, for example. This could have significant implications in the choice of antibiotic necessary to treat a bacterial infection.

SUMMARY OF THE INVENTION

The present invention is directed to the use of oligonucleotide primers specific to nucleic acids characteristic of (typically, genes encoding) certain beta-lactamases. More specifically, the present invention uses primers to identify family specific beta-lactamase nucleic acids (typically, genes) in samples, particularly, in clinical isolates of Gram-negative bacteria. Specific primers of the invention include the primer sequences set forth in SEQ ID NOs: 1–45. As used herein, a nucleic acid characteristic of a beta-lactamase enzyme includes a gene or a portion thereof. A "gene" as used herein, is a segment or fragment of nucleic acid (e.g., a DNA molecule) involved in producing a peptide (e.g., a polypeptide and/or protein). A gene can include regions preceding (upstream) and following (downstream) a coding region (i.e., regulatory elements) as well as intervening sequences (introns, e.g., non-coding regions) between individual coding segments (exons). The term "coding region" is used broadly herein to mean a region capable of being transcribed to form an RNA, the transcribed RNA can be, but need not necessarily be, further processed to yield an mRNA.

Additionally, a method for identifying a beta-lactamase in a clinical sample is provided. Preferably, the clinical sample provided is characterized as a Gram-negative bacteria with resistance to beta-lactam antibiotics. The method includes, providing a pair of oligonucleotide primers, wherein one primer of the pair is complementary to at least a portion of the beta-lactamase nucleic acid in the sense strand and the other primer of each pair is complementary to a different portion of the beta-lactamase nucleic acid in the antisense strand; annealing the primers to the beta-lactamase nucleic acid; simultaneously extending the annealed primers from a 3' terminus of each primer to synthesize an extension product complementary to the strands annealed to each primer wherein each extension product after separation from the beta-lactamase nucleic acid serves as a template for the synthesis of an extension product for the other primer of each pair; separating the amplified products; and analyzing the separated amplified products for a region characteristic of the beta-lactamase.

The method, described above, can employ oligonucleotide primers that are specific for nucleic acid of the TEM family of beta-lactamases, the K1 beta-lactamases, the PSE family of beta-lactamases, and the SHV family of beta-lactamases. Additional primers that can be used include those that are specific for nucleic acid of the AmpC beta-lactamases found in *Enterobacter cloacae, Citrobacter freundii, Serratia marcescens, Pseudomonas aeruginosa*, and *E. coli*.

Still other oligonucleotide primers that are suitable for use in the method of the present invention include primers that are specific for nucleic acid of the plasmid-mediated AmpC beta-lactamases designated as FOX-1, FOX-2, or MOX-1; primers specific for nucleic acid of the OXA-9 beta-lactamase; primers specific for nucleic acid of the OXA-12 beta-lactamase; primers specific for the nucleic acid group of OXA beta-lactamases representing OXA-5, 6, 7, 10, 11, 13, and 14 beta-lactamases; primers specific for the OXA-1 beta-lactamases; and primers specific for nucleic acid of the group of OXA beta-lactamases representing OXA-2, 3, and 15 beta-lactamases.

DETAILED DESCRIPTION OF PREFERRED EMBODIMENTS

The present invention is directed to the detection of nucleic acid that is characteristic of (e.g., at least a segment of a gene that codes for) family-specific beta-lactamase nucleic acid in samples (e.g., clinical isolates of Gram-negative bacteria). Specifically, the present invention is directed to the detection of beta-lactamase nucleic acid (preferably, a gene or at least a segment of a gene) using unique primers and the polymerase chain reaction. Using the primers and methods of the present invention, beta-lactamases belonging to Bush groups 1 (AmpC) and 2 (TEM-1, TEM-2, SHV-1, IRTs, K1), for example, can be identified.

The primers and methods of the present invention are useful for a variety of purposes, including, for example, the identification of the primary beta-lactamase(s) responsible for resistance to third generation cephalosporins among Gram-negative bacteria such as *Escherichia coli* and *Klebsiella pneumoniae* (Thomson et al., *Antimicrob. Agents Chemother* 36(9):1887–1882 (1992)). Other sources of beta-lactamases include, for example, a wide range of *Enterobacteriaceae*, including *Enterobacter* spp., *Citrobacter freundii*, *Morganella morganii*, *Providencia* spp., and *Serratia marcescens* (Jones, *Diag. Microbiol. Infect. Disease* 31(31):461–466 (1998)). Additional beta-lactamase gene sources include *Pseudomonas aeruginosa* (Patrice et al., *Antimicrob. Agents Chemother* 37(5):962–969 (1993)); *Proteus mirabilis* (Bret et al.,*Antimicrob. Agents Chemother* 42(5):1110–1114 (1998)); *Yersinia enterocolitica* (Barnaud et al., *FEMS Microbiol. Letters* 148(1):15–20 (1997)); and *Klebsiella oxytoca* (Marchese et al., *Antimicrob. Agents Chemother* 42(2) 464–467 (1998)).

The methods of the present invention involve the use of the polymerase chain reaction sequence amplification method (PCR) using novel primers. U.S. Pat. No. 4,683,195 (Mullis et al.) describes a process for amplifying, detecting, and/or cloning nucleic acid. Preferably, this amplification method relates to the treatment of a sample containing nucleic acid (typically, DNA) of interest from bacteria, particularly Gram-negative bacteria, with a molar excess of an oligonucleotide primer pair, heating the sample containing the nucleic acid of interest to yield two single-stranded complementary nucleic acid strands, adding the primer pair to the sample containing the nucleic acid strands, allowing each primer to anneal to a particular strand under appropriate temperature conditions that permit hybridization, providing a molar excess of nucleotide triphosphates and polymerase to extend each primer to form a complementary extension product that can be employed in amplification of a desired nucleic acid, detecting the amplified nucleic acid, and analyzing the amplified nucleic acid for a size specific amplicon (as indicated below) characteristic of the specific beta-lactamase of interest. This process of heating, annealing, and synthesizing is repeated many times, and with each cycle the desired nucleic acid increases in abundance. Within in a short period of time, it is possible to obtain a specific nucleic acid, e.g., a DNA molecule, that can be readily purified and identified.

The oligonucleotide primer pair includes one primer that is substantially complementary to at least a portion of a sense strand of the nucleic acid and one primer that is substantially complementary to at least a portion of an antisense strand of the nucleic acid. The process of forming extension products preferably involves simultaneously extending the annealed primers from a 3' terminus of each primer to synthesize an extension product that is complementary to the nucleic acid strands annealed to each primer wherein each extension product after separation from the beta-lactamase nucleic acid serves as a template for the synthesis of an extension product for the other primer of each pair. The amplified products are preferably detected by size fractionization using gel electrophoresis. Variations of the method are described in U.S. Pat. No. 4,683,194 (Saiki et al.). The polymerase chain reaction sequence amplification method is also described by Saiki et al., *Science*, 2, 1350–1354 (1985) and Scharf et al., *Science*, 324, 163–166 (1986).

An "oligonucleotide," as used herein, refers to a polymeric form of nucleotides of any length, either ribonucleotides or deoxyribonucleotides. The term oligonucleotide refers particularly to the primary structure, and thus includes double and single-stranded DNA molecules and double and single-stranded RNA molecules.

A "primer," as used herein, is an oligonucleotide that is complementary to at least a portion of nucleic acid of interest and, after hybridization to the nucleic acid, may serve as a starting-point for the polymerase chain reaction. The terms "primer" or "oligonucleotide primer," as used herein, further refer to a primer, having a nucleotide sequence that possess a high degree of nucleic acid sequence similarity to at least a portion of the nucleic acid of interest. "High degree" of sequence similarity refers to a primer that typically has at least about 80% nucleic acid sequence similarity, and preferably about 90% nucleic acid sequence similarity. Sequence similarity may be determined, for example, using sequence techniques such as GCG FastA (Genetics Computer Group, Madison, Wis.), MacVector 4.5 (Kodak/IBI software package) or other suitable sequencing programs or methods known in the art.

The terms "complement" and "complementary" as used herein, refer to a nucleic acid that is capable of hybridizing to a specified nucleic acid molecule under stringent hybridization conditions. Stringent hybridization conditions include, for example, temperatures from about 50° C. to about 65° C., and magnesium chloride ($MgCl_2$) concentrations from about 1.5 millimolar (mM) to about 2.0 mM. Thus, a specified DNA molecule is typically "complementary" to a nucleic acid if hybridization occurs between the specified DNA molecule and the nucleic acid. "Complementary," further refers to the capacity of purine and pyrimidine nucleotides to associate through hydrogen bonding in double stranded nucleic acid molecules. The following base pairs are complementary: guanine and cytosine; adenine and thymine; and adenine and uracil.

As used herein, the terms "amplified molecule," "amplified fragment," and "amplicon" refer to a nucleic acid molecule (typically, DNA) that is a copy of at least a portion of the nucleic acid and its complementary sequence. The copies correspond in nucleotide sequence to the original molecule and its complementary sequence. The amplicon can be detected and analyzed by a wide variety of methods. These include, for example, gel electrophoresis, single strand conformational polymorphism (SSCP), restriction fragment length polymorphism (RFLP), capillary zone electrophoresis (CZE), and the like. Preferably, the amplicon can be detected, and hence, the type of beta-lactamase identified, using gel electrophoresis and appropriately sized markers, according to techniques known to one of skill in the art.

The primers are oligonucleotides, either synthetic or naturally occurring, capable of acting as a point of initiating synthesis of a product complementary to the region of the DNA molecule containing the beta-lactamase of interest. The primer includes nucleotides capable of hybridizing under stringent conditions to at least a portion of at least one strand of a nucleic acid molecule of a given beta-lactamase.

Preferably, the primers of the present invention typically have at least about 15 nucleotides. Preferably, the primers have no more than about 35 nucleotides, and more preferably, no more than about 22 nucleotides. The primers are chosen such that they preferably produce a primed product of about 200–1100 base pairs.

Optionally, a primer used in accordance with the present invention includes a label constituent. The label constituent can be selected from the group of an isotopic label, a fluorescent label, a polypeptide label, and a dye release compound. The label constituent is typically incorporated in the primer by including a nucleotide having the label attached thereto. Isotopic labels preferably include those compounds that are beta, gamma, or alpha emitters, more preferably isotopic labels are selected from the group of $^{32}$P, $^{35}$S, and $^{125}$I. Fluorescent labels are typically dye compounds that emit visible radiation in passing from a higher to a lower electronic state, typically in which the time interval between adsorption and emission of energy is relatively short, generally on the order of about $10^{-8}$ to about $10^{-3}$ second. Suitable fluorescent compounds that can be utilized include fluorescien and rhodamine, for example. Suitable polypeptide labels that can be utilized in accordance with the present invention include antigens (e.g., biotin, digoxigenin, and the like) and enzymes (e.g., horse radish peroxidase). A dye release compound typically includes chemiluminescent systems defined as the emission of absorbed energy (typically as light) due to a chemical reaction of the components of the system, including oxyluminescence in which light is produced by chemical reactions involving oxygen.

Preferred examples of these primers, that are specific for certain beta-lactamases, are as follows, wherein "F" in the designations of the primers refers to a 5' upstream primer and "R" refers to a 3' downstream primer. For those beta-lactamases that have more than one upstream primer and more than one downstream primer listed below as preferred primers, various combinations can be used. Typically, hybridization conditions utilizing primers of the invention include, for example, a hybridization temperature of about 50° C. to about 60° C., and a MgCl$_2$ concentration of about 1.5 mM (millimolar) to about 2.0 mM. Although lower temperatures and higher concentrations of MgCl$_2$ can be employed, this may result in decreased primer specificity.

The following primers are specific for nucleic acid characteristic of the TEM family of beta-lactamase enzymes.

| Primer Name: | TEMprime2R |
|---|---|
| Primer Sequence: | 5'-TGC TTA ATC AGT GAG GCA CC-3' (SEQ ID NO:1) |
| Primer Name: | TEMprime1F |
| Primer Sequence: | 5'-AGA TCA GTT GGG TGC ACG AG-3' (SEQ ID NO:2) |
| Primer Name: | TEMprimeEndR |
| Primer Sequence: | 5'-CTT GGT CTG ACA GTT ACC-3' (SEQ ID NO:3) |
| Primer Name: | TEMprime2F |
| Primer Sequence: | 5'-TGT CGC CCT TAT TCC-3' (SEQ ID NO:4) |
| Primer Name: | TEMprime15F |
| Primer Sequence: | 5'-TCG GGG AAA TGT GCG-3' (SEQ ID NO:5) |

Employing a primer pair containing the primer sequences of SEQ ID NO:1 and SEQ ID NO:2 to a sample known to contain a TEM family beta-lactamase, a size-specific amplicon of 750 base pairs will typically be obtained. Employing a primer pair containing the primer sequences of SEQ ID NO:3 and SEQ ID NO:5 to a sample known to contain a TEM family beta-lactamase, a size-specific amplicon of 992 base pairs will typically be obtained.

The following primers are specific for nucleic acid characteristic of the SHV family of beta-lactamase enzymes.

| Primer Name: | SHVprime3R |
|---|---|
| Primer Sequence: | 5'-ATC GTC CAC CAT CCA CTG CA-3' (SEQ ID NO:6) |
| Primer Name: | SHVprime2F |
| Primer Sequence: | 5'-GGG AAA CGG AAC TGA ATG AG-3' (SEQ ID NO:7) |
| Primer Name: | SHVprime1R |
| Primer Sequence: | 5'-TAG TGG ATC TTT CGC TCC AG-3' (SEQ ID NO:8) |
| Primer Name: | SHVprime4R |
| Primer Sequence: | 5'-GCT CTG CTT TGT TAT TC-3' (SEQ ID NO:9) |
| Primer Name: | SHVprime1F |
| Primer Sequence: | 5'-CAC TCA AGG ATG TAT TGT G-3' (SEQ ID NO:10) |
| Primer Name: | SHVprimeEndR |
| Primer Sequence: | 5'-TTA GCG TTG CCA GTG CTC G-3' (SEQ ID NO:11) |

Employing a primer pair containing the primer sequences of SEQ ID NO:7 and SEQ ID NO: 11 to a sample known to contain a SHV family beta-lactamase, a size-specific amplicon of 383 base pairs will typically be obtained.

The following primers are specific for nucleic acid characteristic of the AmpC beta-lactamase enzyme (both chromosomal and plasmid-mediated) found in *Enterobacter cloacae*.

| Primer Name: | EcloC3R |
|---|---|
| Primer Sequence: | 5'-GGA ACA GAC TGG GCT TTC ATC-3' (SEQ ID NO:12) |
| Primer Name: | EcloC4F |
| Primer Sequence: | 5'-GGA CAT CCC CTT GAC-3' (SEQ ID NO:13) |
| Primer Name: | EcloC2R |
| Primer Sequence: | 5'-GTG GAT TCA CTT CTG CCA CG-3' (SEQ ID NO:14) |
| Primer Name: | EcloC1F |
| Primer Sequence: | 5'-CTT CTG GCA TGC CCT ATG AG-3' (SEQ ID NO:15) |
| Primer Name: | EcloCR |
| Primer Sequence: | 5'-CAT GAC CCA GTT CGC CAT ATC CTG-3' (SEQ ID NO:16) |
| Primer Name: | EcloCF |
| Primer Sequence: | 5'-ATT CGT ATG CTG GAT CTC GCC ACC-3' (SEQ ID NO:17) |
| Primer Name: | EccKF |
| Primer Sequence: | 5'-CGA ACG AAT CAT TCA GCA CCG-3' (SEQ ID NO:44) |
| Primer Name: | EccKR |
| Primer Sequence: | 5'-CGG CAA TGT TTT ACT GTA GCG CC-3' (SEQ ID NO:45) |

Employing a primer pair containing the primer sequences of SEQ ID NO:14 and SEQ ID NO:15 to a sample known to contain an AmpC beta-lactamase found in *Enterobacter cloacae*, a size-specific amplicon of 416 base pairs will typically be obtained. Employing a primer pair containing the primer sequences of SEQ ID NO:16 and SEQ ID NO:17 to a sample known to contain an AmpC beta-lactamase found in *Enterobacter cloacae*, a size-specific amplicon of 396 base pairs will typically be obtained. Employing a primer pair containing the primer sequences of SEQ ID NO:14 and SEQ ID NO:17 to a sample known to contain an AmpC beta-lactamase found in *Enterobacter cloacae*, a size-specific amplicon of 601 base pairs will typically be obtained. Employing a primer pair containing the primer sequences of SEQ ID NO:17 and SEQ ID NO: 45 to a sample known to contain an AmpC beta-lactamase found in *Enterobacter cloacae*, a size-specific amplicon of 688 base pairs will typically be obtained. Employing a primer pair containing the primer sequences of SEQ ID NO: 44 and SEQ ID NO: 45 to a sample known to contain an AmpC beta-lactamase found in *Enterobacter cloacae*, a size-specific amplicon of 1529 base pairs will typically be obtained.

The following primers are specific for nucleic acid characteristic of the AmpC beta-lactamase enzyme (both chromosomal and plasmid-mediated) found in *Citrobacter freundii*. Although these primers cross-react with the chromosomal AmpC from *E. coli*, the band produced from the *E. coli* AmpC is much larger. Thus, the primers can be used to differentially identify *Citrobacter* from *E. coli*.

| Primer Name: | CFC1F |
|---|---|
| Primer Sequence: | 5'-CTG GCA ACC ACA ATG GAC TCC G-3' (SEQ ID NO:18) |
| Primer Name: | CFC1R |
| Primer Sequence: | 5'-GCC AGT TCA GCA TCT CCC AGC C-3' (SEQ ID NO:19) |

Employing a primer pair containing the primer sequences of SEQ ID NO:18 and SEQ ID NO:19 to a sample known to contain an AmpC beta-lactamase found in *Citrobacter freundii*, a size-specific amplicon of 419 base pairs will typically be obtained.

The following primers are specific for nucleic acid characteristic of the AmpC beta-lactamase enzyme (both chromosomal and plasmid-mediated) found in *Serratia marcescens*.

| Primer Name: | SMC1F |
|---|---|
| Primer Sequence: | 5'-CGT GAC CAA CAA CGC CCA GC-3' (SEQ ID NO:20) |
| Primer Name: | SMC1R |
| Primer Sequence: | 5'-CCA GAT AGC GAA TCA GAT CGC-3' (SEQ ID NO:21) |

Employing a primer pair containing the primer sequences of SEQ ID NO:20 and SEQ ID NO:21 to a sample known to contain an AmpC beta-lactamase found in *Serratia marcescens*, a size-specific amplicon of 335 base pairs will typically be obtained.

The following primers are specific for nucleic acid characteristic of the plasmid-mediated AmpC beta-lactamase enzyme designated as FOX-1, FOX-2, MOX-1, and others in this family.

| Primer Name: | FOX1F |
|---|---|
| Primer Sequence: | 5'-CCA GCC GAT GCT CAA GGA G-3' (SEQ ID NO:22) |
| Primer Name: | FOX1R |
| Primer Sequence: | 5'-CAC GAA CGC CAC ATA GGC G-3' (SEQ ID NO:23) |

Employing a primer pair containing the primer sequences of SEQ ID NO:22 and SEQ ID NO:23 to a sample known to contain a plasmid-mediated AmpC beta-lactamase, such as FOX-1, FOX-2, and MOX-1, a size-specific amplicon of 937 base pairs will typically be obtained.

The following primers are specific for nucleic acid characteristic of the AmpC beta-lactamase enzyme (chromosomal) found in *Pseudomonas aeruginosa*.

| Primer Name: | PaerugR |
|---|---|
| Primer Sequence: | 5'-GGC ATT GGG ATA GTT GCG GTT G-3' (SEQ ID NO:24) |
| Primer Name: | PaerugF |
| Primer Sequence: | 5'-TTA CTA CAA GGT CGG CGA CAT GAC C-3' (SEQ ID NO:25) |

Employing a primer pair containing the primer sequences of SEQ ID NO:24 and SEQ ID NO:25 to a sample known to contain an AmpC beta-lactamase found in *Pseudomonas aeruginosa*, a size-specific amplicon of 268 base pairs will typically be obtained.

The following primers are specific for nucleic acid characteristic of the AmpC beta-lactamase enzyme (both chromosomal and plasmid-mediated) found in *E. coli*.

| Primer Name: | ECOLI C1F |
|---|---|
| Primer Sequence: | 5'-GGA TCA CAC TAT TAC ATC TCG C-3' (SEQ ID NO:26) |
| Primer Name: | ECOLI C1R |
| Primer Sequence: | 5'-CGT ATG GTT GAG TTT GAG TGG C-3' (SEQ ID NO:27) |

Employing a primer pair containing the primer sequences of SEQ ID NO:26 and SEQ ID NO:27 to a sample known to contain an AmpC beta-lactamase found in *E. coli.*, a size-specific amplicon of 254 base pairs will typically be obtained.

The following primers are specific for nucleic acid characteristic of the K1 beta-lactamase enzyme.

| Primer Name: | TOHO-1F |
|---|---|
| Primer Sequence: | 5'-GCG ACC TGG TTA ACT ACA ATC CC-3' (SEQ ID NO:28) |
| Primer Name: | TOHO-1R |
| Primer Sequence: | 5'-CGG TAG TAT TGC CC TTA AGC C-3' (SEQ ID NO:29) |
| Primer Name | MEN-1F |
| Primer Sequence: | 5'-CGG AAA AGC ACG TCG ATG GG-3' (SEQ ID NO:30) |
| Primer Name: | MEN-1R |
| Primer Sequence: | 5'-GCG ATA TCG TTG GTG GTG CC-3' (SEQ ID NO:31) |

Employing a primer pair containing the primer sequences of SEQ ID NO:28 and SEQ ID NO:29 to a sample known to contain a K1 beta-lactamase, a size-specific amplicon of 351 base pairs will typically be obtained. Employing a primer pair containing the primer sequences of SEQ ID NO:30 and SEQ ID NO:31 to a sample known to contain a K1 beta-lactamase, a size-specific amplicon of 415 base pairs will typically be obtained.

The following primers are specific for nucleic acid characteristic of the PSE family of beta-lactamase enzymes.

| | |
|---|---|
| Primer Name: | PSE 1F |
| Primer Sequence: | 5'-CTC GAT GAT GCG TGC TTC GC-3' (SEQ ID NO:32) |
| Primer Name: | PSE 1R |
| Primer Sequence: | 5'-GCG ACT GTG ATG TAT AAA CG-3' (SEQ ID NO:33) |

Employing a primer pair containing the primer sequences of SEQ ID NO:32 and SEQ ID NO:33 to a sample known to contain a PSE1, PSE4, and/or CARB3 beta-lactamase, a size-specific amplicon of 523 base pairs will typically be obtained. If a PSE2 (OXA10) beta-lactamase is present in the sample, it is possible that some cross-reactivity with the primer pair may occur.

The following primers are specific for nucleic acid characteristic of the OXA-9 beta-lactamase enzyme.

| | |
|---|---|
| Primer Name: | OXA 91F |
| Primer Sequence: | 5'-CGT CGC TCA CCA TAT CTC CC-3' (SEQ ID NO:34) |
| Primer Name: | OXA 91R |
| Primer Sequence: | 5'-CCT CTC GTG CTT TAG ACC CG-3' (SEQ ID NO:35) |

Employing a primer pair containing the primer sequences of SEQ ID NO:34 and SEQ ID NO:35 to a sample known to contain a OXA-9 beta-lactamase, a size-specific amplicon of 315 base pairs will typically be obtained.

The following primers are specific for nucleic acid characteristic of the OXA-12 beta-lactamase enzyme.

| | |
|---|---|
| Primer Name: | OXA121F |
| Primer Sequence: | 5' - CGC TGG GAA ACC TAT TCG G - 3' (SEQ ID NO: 36) |
| Primer Name: | OXA121R |
| Primer Sequence: | 5' - CTG CCA TCC AGT TTC TTC GGG - 3' (SEQ ID NO: 37) |

Employing a primer pair containing the primer sequences of SEQ ID NO:36 and SEQ ID NO:37 to a sample known to contain a OXA-12 beta-lactamase, a size-specific amplicon of 341 base pairs will typically be obtained.

The following primers are specific for nucleic acid characteristic of the OXA-5, 6, 7, 10, 11, 13, and 14 beta-lactamase enzymes.

| | |
|---|---|
| Primer Name: | OXA 711F1 |
| Primer Sequence: | 5' - GGT GGC ATT GAC AAA TTC TGG - 3' (SEQ ID NO: 38) |
| Primer Name: | OXA 711B2 |
| Primer Sequence: | 5' - CCC ACC ATG CGA CAC CAG - 3' (SEQ ID NO: 39) |

Employing a primer pair containing the primer sequences of SEQ ID NO:38 and SEQ ID NO:39 to a sample known to contain an OXA-5, 6, 7, 10, 11, 13 or 14 beta-lactamase, a size-specific amplicon of 226 base pairs will typically be obtained.

The following primers are specific for nucleic acid characteristic of the OXA-1 beta-lactamase enzyme.

| | |
|---|---|
| Primer Name: | OXA 1 F2 |
| Primer Sequence: | 5' - TGT GCA ACG CAA ATG GCA C - 3' (SEQ ID NO: 40) |
| Primer Name: | OXA1B14 |
| Primer Sequence: | 5' - CGA CCC CAA GTT TCC TGT AAG TG - 3' (SEQ ID NO: 41) |

Employing a primer pair containing the primer sequences of SEQ ID NO:40 and SEQ ID NO:41 to a sample known to contain a OXA-1 beta-lactamase, a size-specific amplicon of 579 base pairs will typically be obtained.

The following primers are specific for nucleic acid characteristic of the OXA-2, 3, and 15 beta-lactamase enzymes.

| | |
|---|---|
| Primer Name: | OXA 23 F1 |
| Primer Sequence: | 5' - AGG CAC GAT AGT TGT GGC AGA C - 3' (SEQ ID NO: 42) |
| Primer Name: | 0XA23B3 |
| Primer Sequence: | 5' - CAC TCA ACC CAT CCT ACC CAC C - 3' (SEQ ID NO: 43) |

Employing a primer pair containing the primer sequences of SEQ ID NO:42 and SEQ ID NO:43 to a sample known to contain a OXA-2, 3 or 15 beta-lactamase, a size-specific amplicon of 555 base pairs will typically be obtained.

Various other primers, or variations of the primers described above, can also be prepared and used according to methods of the present invention. For example, alternative primers can be designed based on targeted beta-lactamases known or suspected to contain regions possessing high G/C content (i.e., the percentage of guanine and cytosine residues). As used herein, a "high G/C content" in a target nucleic acid, typically includes regions having a percentage of guanine and cytosine residues of about 60% to about 90%. Thus, changes in a prepared primer will alter, for example, the hybridization or annealing temperatures of the primer, the size of the primer employed, and the sequence of the specific resistance gene or nucleic acid to be identified. Therefore, manipulation of the G/C content, e.g., increasing or decreasing, of a primer or primer pair may be beneficial in increasing detection sensitivity in the method.

Additionally, depending on the suspected nucleic acid in the sample, a primer of the invention can be prepared that varies in size. Typically, primers of the invention are about 12 nucleotides to about 50 nucleotides in length, preferably the primers are about 15 nucleotides to about 25 nucleotides in length. Oligonucleotides of the invention can readily be synthesized by techniques known in the art (see, for example, Crea et al., *Proc. Natl. Acad. Sci.* (U.S.A.) 75:5765 (1978)).

Once the primers are designed, their specificity can be tested using the following method. Depending on the target nucleic acid of clinical interest, a nucleic acid is isolated from a bacterial control strain known to express or contain the resistance gene. This control strain, as used herein, refers to a "positive control" nucleic acid (typically, DNA). Additionally, a "negative control" nucleic acid (typically, DNA) can be isolated from one or more bacterial strains known to express a resistance gene other than the target gene of interest. Using the polymerase chain reaction, the designed primers are employed in a detection method, as described above, and used in the positive and negative control samples and in at least one test sample suspected of containing the resistance gene of interest. The positive and negative controls provide an effective and qualitative (or grossly quantitative) means by which to establish the presence or the absence of the gene of interest of test clinical samples. It should be recognized that with a small percentage of primer pairs, possible cross-reactivity with other Beta-lactamase genes might be observed. However, the size and/or intensity of any cross-reactive amplified product will be considerably different and can therefore be readily evaluated and dismissed as a negative result.

The invention also relates to kits for identifying a family specific beta-lactamase enzymes by PCR analysis. Kits of the invention typically include one or more primer pairs specific for a beta-lactamase of interest, one or more positive controls, one or more negative controls, and protocol for identification of the beta-lactamase of interest using polymerase chain reaction. A negative control includes a nucleic acid (typically, DNA) molecule encoding a resistant beta-lactamase other that the beta-lactamase of interest. The negative control nucleic acid may be a naked nucleic acid (typically, DNA) molecule or inserted into a bacterial cell. Preferably, the negative control nucleic acid is double stranded, however, a single stranded nucleic acid may be employed. A positive control includes a nucleic acid (typically, DNA) that encodes a beta-lactamase from the family of beta-lactamases of interest. The positive control nucleic acid may be a naked nucleic acid molecule or inserted into a bacterial cell, for example. Preferably, the positive control nucleic acid is double stranded, however, a single stranded nucleic acid may be employed. Typically, the nucleic acid is obtained from a bacterial lysate.

Accordingly, the present invention provides a kit for characterizing and identifying a family specific beta-lactamase that would have general applicability. Preferably, the kit includes a polymerase (typically, DNA polymerase) enzyme, such as Taq polymerase, and the like. A kit of the invention also preferably includes at least one primer pair that is specific for a beta-lactamase. A buffer system compatible with the polymerase enzyme is also included and are well known in the art. Optionally, at least one primer pair may contain a label constituent, a fluorescent label, a polypeptide label, and a dye release compound. The kit may further contain at least one internal sample control, in addition to one or more further means required for PCR analysis, such as a reaction vessel. If required, a nucleic acid from the bacterial sample can be isolated and then subjected to PCR analysis using the provided primer set of the invention.

In another embodiment, family specific beta-lactamase enzymes in clinical samples, particularly clinical samples containing Gram-negative bacteria, can be detected by the primers described herein in a "microchip" detection method. In a microchip detection method, nucleic acid, e.g., genes, of multiple beta-lactamases in clinical samples can be detected with a minimal requirement for human intervention. Techniques borrowed from the microelectronics industry are particularly suitable to these ends. For example, micromachining and photolithographic procedures are capable of producing multiple parallel microscopic scale components on a single chip substrate. Materials can be mass produced and reproducibility is exceptional. The microscopic sizes minimize material requirements. Thus, human manipulations can be minimized by designing a microchip type surface capable of immobilizing a plurality of primers of the invention on the microchip surface.

Thus, an object of the present invention is to provide a parallel screening method wherein multiple serial reactions are automatically performed individually within one reaction well for each of the plurality of nucleic acid strands to be detected in the plural parallel sample wells. These serial reactions are performed in a simultaneous run within each of the multiple parallel lanes of the device. "Parallel" as used herein means wells identical in function. "Simultaneous" means within one preprogrammed run. The multiple reactions automatically performed within the same apparatus minimize sample manipulation and labor.

Thus, the present invention provides multiple reaction wells, the reaction wells being reaction chambers, on a microchip, each reaction well containing an individualized array to be used for detecting a beta-lactamase gene uniquely specified by the substrates provided, the reaction conditions and the sequence of reactions in that well. The chip can thus be used as a method for identifying beta-lactamase genes in clinical samples.

Objects and advantages of this invention are further illustrated by the following examples, but the particular materials and amounts thereof recited in these examples, as well as other conditions and details, should not be construed to unduly limit this invention.

EXAMPLE 1

*Klebsiella pneumoniae* with ESBLs and a Plasmid-Mediated AmpC Beta-Lactamase

Materials and Methods

*Klebsiella pneumoniae* 225

*Klebsiella pneumoniae* 225 was isolated from a 43-year-old white male patient who was working in a New York City sewage canal on 26 April, 1996. While in a pit containing a layer of sewage, a screen fell, knocking the patient down in the sewage. The patient struck his left forehead, sustaining a severe laceration approximately 20 centimeters (cm) long and down to the skull and was unconscious for approximately five minutes. The patient was taken to a local hospital where the wound was surgically debrided, irrigated, and closed. Intravenous cefazolin and gentamicin were administered pre-operatively, and cefazolin was continued 24 hours post-operatively. The patient was discharged and returned to Omaha, Nebr., four days later.

On 2 May 1996, the patient was seen by an Omaha surgeon who diagnosed wound infection, ordered culture of the wound drainage, and initiated therapy with cephalexin and penicillin. The culture yielded growth of *K. pneumoniae, Aeromonas hydrophila* and *Proteus penneri*. By 24 May 1996, the patient was experiencing significant swelling and pain in the left scalp area, significant weakness and dizziness, and a low grade fever. An infectious disease consult was ordered, and the patient was hospitalized for further evaluation and management.

Laboratory findings included a white blood cell count of 21,000 per cubic millimeter (cmm). Aspiration of a bulging left temporal mass from the patient yielded 7 milliliter (ml) of purulent fluid from which *K. pneumoniae* and *A. hydrophila* were cultured.

The patient was empirically treated with piperacillin/tazobactam and ciprofloxacin. On 25 May 1996, the patient had incision drainage and debridement of the wound. Operative findings as well as preoperative CT scan of the patient's head did not reveal osteomyelitis. There was an abscess commencing in the region of the left zygoma and extending superior to the parietal region, with two small opaque foreign bodies in the caudal aspect of the collection. On 27 May 1996, following antibiotic susceptibility results, therapy was changed to imipenem/cilastatin. The drain was removed and the patient was discharged on 29 May 1996, and treated at home with intravenous imipenem/cilastatin via a peripheral inserted central catheter. After four weeks of therapy all signs of inflammation resolved. The patient remained free from infection at follow-up on 10 Dec. 1996.

Susceptibility Tests

Susceptibility tests were performed by microdilution methodology using the MicroScan Walkaway system (Dade MicroScan Inc., Sacramento, Calif.) and by NCCLS microdilution methodology in Mueller-Hinton broth (CM 405, Oxoid, Basingstoke, England) using an inoculum of approximately $5 \times 10^5$ CFU/ml (National Committee for Clinical Laboratory Standards, 1997, Approved Standard M7-A4) and also by NCCLS disk diffusion methodology (National Committee for Clinical Laboratory Standards, 1997, Approved Standard M2-A6).

Clavulanate Double-Disk Potentiation Test

Using the procedure of Brun-Buisson et al., Lancet., ii, 302–306 (1987), a Mueller-Hinton agar plate (CM 337, Oxoid, Basingstoke, England) was inoculated with K. pneumoniae 255 as for a standard disk diffusion test. Disks (BBL, Cockeysville, Md.) containing aztreonam, cefotaxime, ceftriaxone, and ceftazidime were strategically placed around an amoxicillin-clavulanate disk prior to incubation at 35° C. ESBL production was inferred by the presence of characteristic distortions of the inhibition zone indicative of clavulanate potentiation of the test drug.

Three-Dimensional Test

Using a modification of the procedure of Thomson and Sanders, Antimicrob. Agents Chemother., 36:1877–1882 (1992), the surface of a Mueller-Hinton agar plate was inoculated with E. coli ATCC 25922 as for a standard disk diffusion test. A slit made in the agar with a sterile no. 11 scalpel blade was then inoculated with a heavy suspension of cells of K. pneumoniae 225 that had been grown to logarithmic phase in 10 ml tryptone soy broth (CM 129, Oxoid), centrifuged, and resuspended in 100 microliter ($\mu$l) TRIS EDTA buffer (T-9285 Sigma Chemical Co., St. Louis, Mo.) for 40 minutes. Disks containing aztreonam, cefotaxime, ceftriaxone, ceftazidime and cefoxitin were placed on the agar 3 millimeters (mm) away from the inoculated slit, and the plate was incubated in the usual manner.

Enzymatic inactivation of the antibiotics was inferred if the margin of the inhibition zone was distorted in the vicinity of the slit in a manner that indicated loss of drug activity (hydrolysis) as the drug diffused through the inoculated slit.

Isoelectric Focusing, Cefotaxime Hydrolysis, and Inhibitor Determinations

Using a modification of the methods of Sanders et al., Antimicrob. Agents Chemother., 30:951–952 (1986), Bauernfeind et al., Infection, 18;294–298 (1990), and Thomson et al., Antimicrob. Agents Chemother., 35;1001–1003 (1991), sonic extracts of K. pneumoniae 225 and strains of E. coli that produced reference beta-lactamases, were characterized by determining the isoelectric focusing point (pI) of each beta-lactamase, inhibitor profile in the presence and absence of 1,000 micromolar ($\mu$M) clavulanate and 1,000 $\mu$M cloxacillin, and ability to hydrolyze 0.75 $\mu$g/ml cefotaxime solution.

Plasmid Isolations

Plasmid DNA isolated using alkaline lysis (Manniatis et al., Molecular Cloning: A Laboratory Manual, Cold Spring Harbor, N.Y., 1982) was performed with the following modifications. Cell pellets were washed twice with 3% TRITON-X 100 dissolved in Tris-ethylene diaminetetraacetate (Tris-EDTA) (pH 8). After neutralization, supernatant was extracted with phenol plus 1/10 volume 10% sodium dodecyl sulfate (SDS) followed by one extraction using phenol:chloroform:isoamyl alcohol (25:24:1) followed by one or more chloroform:isoamyl (24:1) extractions until supernatant was clear. When designated, some samples were treated with plasmid-safe DNase (Epicentre Technologies, Madison, Wis.) as described by the manufacturer. Plasmid DNA was electrophoresed on the day of preparation to decrease the possibility of DNA damage (nicking) during storage. Plasmids were separated by agarose (0.8%) gel electrophoresis using 1×Tris-acetate-EDTA (TAE) as the buffer system.

In some cases, plasmids were visualized without previous isolation by lysing the bacterial cells within the well of the agarose gel. One colony of Klebsiella pneumoniae 225 was suspended into 5 $\mu$l of protoplasting buffer (30 mM Tris-HCl (pH 8), 5 mM EDTA, 50 mM NaCl, 20% weight by volume (w/v) sucrose, 50 $\mu$g/ml RNase A and 50 $\mu$g/ml lysozyme; the RNase A and lysozyme added just prior to use) and incubated 30 minutes at 37° C. Into each well of the agarose gel, 2 $\mu$l of room temperature lysis buffer (89 mM Tris (pH 8.3), 89 mM boric acid, 25 mM EDTA, 2% w/v SDS, 5% w/v sucrose and 0.04% Bramaphenol blue) was loaded just prior to the addition of protoplast suspension. The protoplast suspension was loaded and the gel was run for 15 minutes at 30 volts to lyse the protoplasts. After 15 minutes the voltage was increased to 120 volts and the gel was run for 1–1.5 hours. Before staining in ethidium bromide (0.5 $\mu$g/ml), the gel was washed in large volumes of water with at least two changes to remove the SDS. The plasmid bands were visualized with a UV transilluminator. The gel consisted of 4.8% agarose, 1×Tris-borate-EDTA (TBE) (89 mM Tris, 89 mM boric acid, and 2.5 mM EDTA) (pH 8.3) and 10% SDS. The running buffer was 1×TBE plus 10% SDS.

Southern Analysis

Plasmid DNA was prepared by alkaline lysis separated as described above. To achieve high resolution separation, gels were electrophoresed for 17–18 hours at 35 volts. DNA was transferred using 0.4 M NaOH to Zeta-Probe blotting membranes using a vacuum blotter (Bio-RAD) as described by the manufacturer. TEM specific probes (5'-TGCTTAATCAGTGAGGCACC-3' (SEQ ID NO:1) nucleotides 1062–1042; numbering of Sutcliff, Proc. Nat. Aca. Sci. USA, 75:3737–3741 (1978)) and SHV (5'-TTAGCGTTGCCAGTGCTCG-3' (SEQ ID NO:11 nucleotides 988–970; numbering of Mercier et al., Antimicrob. Agents Chemother., 34:1577–1583 (1990)) were labeled using the Genius System Oligonucleotide 3'-End labeling kit (Boehringer Mannheim, Indianapolis, Ind.). Prehybridization and hybridization followed the recommendation of the manufacturer using 1% SDS at 37° C. Initially, blots were washed with 5×SSC (twice at room temperature for 5 minutes and twice at room temperature for 30 minutes followed by washings using tetramethylammonium chloride (TMAC); once at 37° C. for 15 minutes and twice at 48° C. for 20 minutes. Labeled probe hybridized to plasmid DNA was detected using the Genius Luminescent detection kit (Boehringer Mannheim) as described by manufacturer.

Polymerase Chain Reaction (PCR)

Template was prepared as below in Example 3. Primers used for amplification are listed in Table 1.

TABLE 1

PCR Primers

| Beta-lactamase Gene | Sequence (nucleotide, nt) |
|---|---|
| TEM[1] | (Forward) 5'-AGATCAGTTGGGTGCACGAG-3' (nt 313–332) (SEQ ID NO: 2) <br> (Reverse) 5'-TGCTTAATCAGTGAGGCACC-3' (nt 1061–1042) (SEQ ID NO: 1) |
| SHV[2] | (Forward) 5'-GGGAAACGGAACTGAATGAG-3' (nt 606–625) (SEQ ID NO: 7) <br> (Reverse) 5'-ATCGTCCACCATCCACTGCA-3' (nt 757–738) (SEQ ID NO: 6) |
| OXA-9[3] | (Forward) 5'-CGTCGCTCACCATATCTCCC-3' (nt 2783–2802) (SEQ ID NO: 34) <br> (Reverse) 5'-CCTCTCGTGCTTTAGACCCG-3' (nt 3097–3078) (SEQ ID NO: 35) |
| Enterobacter AmpC[4] | (Forward) 5'-ATTCGTATGCTGGATCTCGCCACC-3' (nt 413–436) (SEQ ID NO: 17) <br> (Reverse) 5'-CATGACCCAGTTCGCCATATCCTG-3' (nt 808–785) (SEQ ID NO: 16) |

1: Sequence Reference = Sutcliffe et al., Proc. Nat. Aca. Sci. USA, 75, 3737–3741 (1978).
2: Sequence Reference = Mercier et al., Antimicrob. Agents Chemother., 34 1577–1583 (1990).
3: Sequence Reference = Tolmasky et al., Plasmid, 24, 218–226 (1990).
4: Sequence Reference = Galleni et al., Biochem. J., 250, 753–760 (1988).

PCR amplifications were carried out as described below in Example 3 with the following modifications. The composition of the reaction mixture was 10 mM Tris-HCl (pH 8.3), 50 mM KCl, 1.5 mM $MgCl_2$, 0.2 mM (each) of the four deoxynucleoside triphosphates, and 1.2 U of Taq polymerase (GIBCO, Gaithersburg, Md.) in a total volume of 48 $\mu$l. A total of 2 $\mu$l of sample lysate containing the DNA template was added to the reaction mixture. The PCR parameters consisted of initial denaturation step at 95° C. for 5 minutes followed by 24 amplification cycles consisting of a denaturation step of 96° C. for 15 seconds; primer annealing at 55° C. for 15 seconds and extension at 72° C. for 2 minutes. Amplified product was detected by agarose (2%) gel electrophoresis using a 1×TAE buffering system. Some of the PCR products were sequenced by automated PCR cycle-sequencing with dye-terminator chemistry using a DNA stretch sequencer from Applied Biosystems (Foster City, Calif.).

Restriction Fragment Length Polymorphism (RFLP)

SHV-specific PCR products (⅕ volume) were used directly in a restriction endonuclease assay (Nyesch-Inderbinen et al., Eur. J. Clin. Microbiol. Infect. Dis. 15:398–402 (1996)) using the restriction endonuclease, NheI (New England Biolabs, Beverly, Mass.). Enzyme reactions were carried out as directed by the manufacturer. To ensure that each sample received the same amount of enzyme, an enzyme mix containing the buffer system and enzyme was aliquoted to each sample. Samples were resolved using 2% agarose and a 1×TAE buffer system.

Transformation and Conjugation

Transformations were done using a modified Hanahan method (TSS) described by CLONTECH (CLONTECH Laboratories, Inc., Palo Alto, Calif., Transformer site. Directed Mutagenesis Kit —2nd version). Plasmids were separated as described above, excised from the gel, and electroeluted from the gel slice. The DNA was transformed into E. coli HB1 $\mu$l.

Conjugation experiments were carried out by filter mating using E. coli, strain C600, as the recipient. Transconjugants were selected on Luria-Bertani agar plates containing 30 $\mu$g/ml of naladixic acid. An endol test was performed on the transconjugant (E. coli C600) to further differentiate it from the donor (K. pneumoniae 225).

Results

Susceptibility Tests

The results of the microdilution tests performed with K. pneumoniae 225 using the NCCLS microdilution methodology were as follows:

MIC>64 $\mu$g/ml: ticarcillin, ticarcillin/clavulanate, piperacillin, piperacillin/tazobactam, ceftazidime, cefixime, loracarbef, cephalothin, cefazolin, cefoxitin, aztreonam, ampicillin/sulbactam MIC 64 $\mu$g/ml: amoxicillin/clavulanate, cefpodoxime MIC 16 $\mu$g/ml: ceftriaxone, cefotaxime MIC 1 $\mu$g/ml: imipenem, cefepime MIC 0.5 $\mu$g/ml: ciprofloxacin MIC 0.06 $\mu$g/ml: meropenem Other susceptibility results obtained in MicroScan tests were (MicroScan MICs shown in parentheses):

Resistant: cefuroxime (>16 m), gentamicin (>8 $\mu$g/m), tobramycin (>8 $\mu$g/ml), amikacin (>32 $\mu$g/ml), trimethoprim/sulfamethoxazole (>2/38), tetracycline (>8 $\mu$g/ml), nitrofurantoin (>64 $\mu$g/ml), chloramphenicol (>16 $\mu$g/ml)

Susceptible: ofloxacin and levofloxacin (both 2 $\mu$g/ml), cefotetan (16 $\mu$g/ml)

Discrepancies between MicroScan and conventional NCCLS results were obtained with ciprofloxacin (0.5 $\mu$g/ml in conventional microdilution test, susceptible by disk test, 2 $\mu$g/ml in MicroScan test) and cefotetan (resistant in disk test with 12 mm zone diameter, susceptible by MicroScan, 16 $\mu$g/ml).

The susceptibility results for the Aeromonas hydrophila isolate were not considered unusual and are not reported.

Double Disk and Three Dimensional Tests

The clavulanate double-disk potentiation test was positive with each of the antibiotics tested, indicating that K. pneumoniae possessed one or more clavulanate-sensitive beta-lactamases capable of hydrolyzing aztreonam, cefotaxime, ceftriaxone, and ceftazidime. This result was consistent with beta-lactamase activity of Bush group 2be or, possibly, high level activity of Bush group 2b.

The three dimensional test was positive for each of the antibiotics tested, aztreonam, cefotaxime, ceftriaxone, ceftazidime, and cefoxitin, indicating β-lactamase-mediated hydrolysis of each drug. The positive result with cefoxitin was notable, being consistent with production of a Bush group 1 beta-lactamase.

Isoelectric Focusing-Based Tests

Isoelectric focusing yielded five beta-lactamase bands with pI values of 5.4, 6.8, 7.6, 8.2, and ³9.0, values consistent with TEM-1 (pI 5.4), PSE-3, OXA-9 or unknown enzyme (pI 6.8), SHV-1, SHV-2, or SHV-8 (pI 7.6), SHV-5 (pI 8.2) and AmpC (pI ³9.0) (Table 2, below). Only the pI ³9.0 enzyme was resistant to clavulanate, confirming that this was a Bush group 1 (AmpC) beta-lactamase. The beta-lactamase bands which hydrolyzed cefotaxime, as detected by microbiological assay, were pI 7.6, pI 8.2, and pI ³9.0. These results suggested the presence of clavulanate-sensitive ESBLs of pI values 7.6 and 8.2, and added support to the identification of an AmpC enzyme with a pI value 39.0. These results are supported and/or confirmed by PCR (see below).

TABLE 2

Isoelectric Focusing

| pI   | Ca Sensitive | Ctx Hydrolyzed | Possible Enzyme |
|------|--------------|----------------|-----------------|
| 5.4  | S            | −              | TEM-1           |
| 6.8  | S            | −              | OXA-9           |
| 7.6  | S            | +              | SHV-1, SHV-2    |
| 8.2  | S            | +/−            | SHV-5           |
| ~9.3 | R            | +              | AmpC            |

Ca = clavulanate (1000 μm)
Ctx = cefotasime (0.75 μg/ml)

Polymerase Chain Reaction (PCR)

PCR analysis was used initially to confirm and/or identify the beta-lactamases observed during isoelectric focusing (Table 2, above). Primer sets specific for the TEM or SHV gene families, *Enterobacter* AmpC, OXA-9 and integron sequences were used in a PCR (Table 1, above). PCR identified the presence of TEM and SHV-like genes, an *Enterobacter* AmpC-like gene, the OXA-9 gene and integron sequences (data not shown).

Plasmids

Multiple plasmid isolations from *K. pneumoniae* 225 revealed the organism carried only two plasmids. Using a supercoiled DNA ladder, the estimated sizes of these plasmids were approximately 17 kb and approximately 90 kb. Three different isolation procedures were used to extract plasmid DNA; alkaline lysis (Manniatis et al., *Molecular Cloning: A Laboratory Manual*, Cold Spring Harbor, N.Y., 1982), lysozymes/SDS (Crosa et al., "Plasmids" In Gerhardt et al., *Manual of Methods for General Bacteriology*, American Society for Microbiology, Washington, D.C., pages 266–282, 1981), and cell lysis and extraction within the well of the gel. All procedures yielded the same two plasmids indicating that plasmids were not being lost during any one type of isolation procedure. Alkaline lysis yielded the purest preparation of plasmid DNA and was therefore used for southern blot analysis. It was possible that residual chromosomal DNA comigrated and therefore masked a possible plasmid. To address this, an enzyme, plasmid-safe DNase (Epicentre Technologies, Madison, Wash.), which does not cleave supercoiled DNA, was used to treat the DNA plasmid preparations before electrophoresis. Treatment with plasmid-safe DNase degraded the chromosomal DNA band while having no effect on the 17 kb and 90 kb plasmids, indicating no other plasmids were present in *K. pneumoniae* 225 (data not shown).

Southern Analysis

It was surprising that an organism expressing 5 and possibly 6 beta-lactamases would have only two extrachromosomal pieces of DNA. Therefore, whether beta-lactamase genes were encoded on one or both plasmids was evaluated. Southern analysis revealed that both the 90 kb and 17 kb plasmid encoded TEM-like genes, however, only the 90 kb plasmid encoded the SHV-like genes (data not shown).

Transformation and Conjugation

It was possible that the plasmid-mediated AmpC gene encoded by *K. pneumoniae* 225 cross-hybridized with the TEM-specific probe and that one or both plasmids encoded the AmpC enzyme observed during isoelectric focusing. In an attempt to isolate each plasmid from the other, transformation experiments were carried out. Each plasmid was extracted and gel purified. The approximately 17 kb plasmid was transformed into *E. coli* HB101, and selected using ampicillin. After confirming that only a 17 kb plasmid was present in the HB101 transformants, a disk diffusion assay was performed (Table 3).

TABLE 3

Disk Diffusion Assay

| | Zone Size (mm) | | |
|---|---|---|---|
| Drug | Kleb 225 | Tr (17 kb) | Tc |
| Chloramphenical | 8 (R) | 22 (S) | 12 (R) |
| Gentomicin | 8 (R) | 25 (S) | 8 (R) |
| Cefotetan | 12 (R) | 30 (S) | 11 (R) |
| Ceftriaxone | 13 (R) | 32 (S) | 12 (R) |
| Cefotaxime | 15 (I) | 34 (S) | 12 (R) |
| Ceftazidime | 8 (R) | 33 (S) | 7 (R) |
| Pippercillin/Tazpbactam | 15 (R) | 30 (S) | 14 (R) |
| Trimethoprim/Sulfamethoxazole | 6 (R) | 31 (S) | 8 (R) |
| Cefoxitin | 6 (R) | 25 (S) | 7 (R) |
| Aztreonam | 8 (R) | 33 (S) | 7 (R) |
| Ciprofloxacin | 22 (S) | 31 (S) | 31 (S) |
| Imipenem | 22 (S) | 33 (S) | 23 (S) |
| Amikacin | — | 12 (R) | — |
| Ampicillin | — | 7 (R) | — |

Tr = transformant
Tc = transconjugate

The transformant did not exhibit diminished susceptibility to any of the drugs in Table 3 except ampicillin and amikacin, indicating that the 17 kb plasmid did not encode AmpC or extended spectrum beta-lactamase genes. Several attempts to transform the large plasmid into *E. coli*, (strains HB101 and MV1190) failed. Transformation using the 90 kb plasmid produced transformants that were resistant only to ampicillin. When plasmid DNA was isolated from these transformants many sized plasmids, all less than 90 kb, were present (data not shown).

The data obtained from the transformation of the 17 kb plasmid suggested that the plasmid-mediated AmpC gene was encoded on the 90 kb plasmid. Therefore, conjugation experiments were performed. Conjugation between *K. pneumoniae* 225 and *E. coli* C600 resulted in the transfer of both the 90 kb and 17 kb plasmids. Cefoxitin resistance of the transconjugant indicated transfer of the AmpC gene (Table 3). Taken together, these data strongly suggest that the AmpC gene is located on the 90 kb plasmid.

Restriction Fragment Length Polymorphism (RFLP)

Some ESBL-SHV enzymes with a pI of 7.6 (SHV-2, SHV-7) contain a glycine to serine amino acid substitution at position 238. In the structural SHV-gene the nucleotide mutation resulting in the amino acid substitution creates a new endonuclease restriction site, NheI. This restriction site is not present in the structural gene of SHV-1, SHV-6, SHV-8, or SHV-11, but these enzymes also have a pI of 7.6. Therefore, RFLP analysis using NheI can help distinguish between these two groups of enzymes (NYesch-Inderbinen et al., *Eur. J. Clin. Microbiol. Infect. Dis.*, 39:185–191 (1996)). Isoelectric focusing data suggested that the identity of the pI 7.6 beta-lactamase could be SHV-2, SHV-6, SHV-8 or a hyperproducer of SHV-1. To help distinguish between SHV-2 and SHV-6, SHV-8 or a hyperproducer of SHV-1, RFLP analysis on SHV-specific PCR products from *K. pneumoniae* 225 were performed using NheI. The presence of the NheI site in the SHV-specific PCR product will result in 2 bands: 219 bp and 164 bp. The absence of the NheI site will result in no cleavage and a full length fragment: 383 bp. SHV-specific PCR products amplified from template prepared from *K. pneumoniae* 225 show both full length and cleaved products. These data suggest that SHV-1, SHV-6, or SHV-8 as well as an SHV ESBL is encoded by *K. pneumoniae* 225 DNA.

EXAMPLE 2

Beta-lactamases Responsible for Resistance to Expanded-Spectrum Cephalosporins Among *Klebsiella pneumoniae, Escherichia coli* and *Proteus mirabilis* Isolates Recovered in South Africa Materials and Methods Bacterial Strains During a period of three months in 1993, 37 strains of *Klebsiella pneumoniae* (13 blood, 5 burn, 7 wound, 11 tracheal isolates), 4 strains of Proteus mirabilis (all wound isolates) and 4 strains of *Escherichia coli* (1 blood, 1 burn, 2 wound isolates) were collected from patients at the following medical centers in South Africa: Tygerberg Hospital near Cape Town, King Edward VIII Hospital in Durban, Chris Hani Baragwanath Hospital in Soweto and Pretoria Academic Hospital in Pretoria. The strains were provided in response to a request for all strains of Enterobacteriaceae, lacking inducible beta-lactamases, that were intermediate or resistant to cefotaxime or ceftazidime. The total number of strains screened is unknown, and at this time the referring hospitals did not perform more sensitive screening tests for ESBL detection. Therefore accurate prevalence data were not obtained.

Thirty-four of the 43 patients involved (including all from whom blood isolates were obtained) had received a third generation cephalosporin during the four weeks prior to isolation of the above organisms. Fifteen patients (including 8 blood isolate patients) were receiving either cefotaxime or ceftazidime at the time the isolates were cultured and were considered not to be responding to these agents.

Susceptibility Testing and Antibiotics

Antibiotic susceptibility was determined by standard disk diffusion (NCCLS Standard M2-T4, 1994) and agar dilution (NCCLS Standard M7-T2, 1994) procedures. Standard powders of antimicrobial agents were kindly provided by the following companies: piperacillin and tazobactam (Lederle Laboratories, Wayne, N.J.); cefoxitin and imipenem, (Merck, Rathway, N.J.); cefotaxime, (Hoechst-Roussel Pharmaceuticals Inc., Somerville, N.J.); ceftazidime, (Glaxo Group Research Ltd., Greenford, England); aztreonam and cefepime, (Bristol-Myers Squibb, Princeton, N.J.). Disks for agar diffusion were obtained from Becton Dickinson Microbiology Systems (Cockeysville, Md.). For quality control purposes, the following quality control strains were run simultaneously with the test organisms *E. coli* ATCC 25922, *Pseudomonas aeruginosa* ATCC 27853, *E. coli* ATCC 35218, and *Staphylococcus aureus* ATCC 29213. Throughout this study, results were interpreted using NCCLS criteria for disk diffusion (NCCLS Standard M2-T4, 1994) and broth dilution (NCCLS Standard M7-T2, 1994).

Double-Disk Test

All the strains were screened for the production of extended-spectrum beta-lactamases by using the double-disk test as described by Jarlier et al., *Rev. Infect. Dis.*, 10:867–878 (1988). A potentiation of the zones of cefotaxime, ceftriaxone, ceftazidime or aztreonam by clavulanic acid represented a positive test and was indicative of possible presence of an extended-spectrum beta-lactamase.

Beta-lactamase Characterization

Overnight cultures in 5 ml trypticase soy broth were diluted with 45 ml fresh broth and incubated with shaking for 4 hours at 37° C. Cells were harvested by centrifugation at 4° C., washed with 1 M potassium-phosphate buffer (pH 7.0), suspended and sonicated. After sonication, crude extracts were obtained by centrifugation at 5,858×g for 1 hour. One strain, *K. pneumoniae* Pit 68, with a suspected AmpC beta-lactamase, was induced with cefoxitin as described below in Example 3. The rate of hydrolysis of 100 $\mu$M solutions of nitrocephin, cephalothin, cefotaxime, ceftazidime and aztreonam was performed by spectrophotometric assays on crude beta-lactamase extracts (Palzkill et al., *Antimicrob. Agents Chemother.*, 36:1991–1996 (1992)).

The beta-lactamases in the sonic extracts were assessed for isoelectric points (pIs), general substrate and inhibitor characteristics in polyacrylamide gels. As controls, crude beta-lactamase preparations from the following organisms possessing different TEM and SHV enzymes were examined simultaneously with the *K. pneumoniae*, *E. coli* and *P. mirabilis* strains: TEM-1 [from *E. coli* RTEM (R6K)], TEM-2 [from *E. coli* 1752E (RP1)], TEM-10 [from *E. coli* C600 (pK2)], TEM-26 [from *E. coli* HB101 (pJPQ101), SHV-1 [from *E. coli* J53 (R1010)], SHV-2 [from *Klebsiella ozaenae* 2180], SHV-3 [from *E. coli* J53 (pUD18)], SHV-4 [from *E. coli* J53-2 (pUD21)] and SHV-5 [from *E. coli* ClaNal (pAFF2)].

DNA Amplification Using Polymerase Chain Reaction (PCR)

The organisms were inoculated into 5 ml of Luria Bertani (LB) broth (Difco, Detroit, Mich.) and incubated for 20 hours at 37° C. with shaking. Cells from 1.5 ml of overnight culture were harvested by centrifugation at 17,310×g in an Hermle centrifuge for 5 minutes. After the supernatant was decanted, the pellet was resuspended in 500 $\mu$l of distilled water. The cells were lysed by heating at 95° C. for 10 minutes and cellular debris was removed by centrifugation for 5 minutes at 17,310×g. The supernatant was used as source of template for amplification.

The following oligonucleotide primers specific for the SHV and TEM genes were designed by using MacVector version 4.5 (Kodak/IBI): SHV genes: A [5'-(CACTCAAGGATGTATTGTG)-3'] (SEQ ID NO:10) and B [5'-(TTAGCGTTGCCAGTGCTCG)-3'] (SEQ ID NO:11) corresponding to nucleotide numbers 103 to 121 and 988 to 970, respectively, of Mercier et al., *Antibicrob. Agents Chemother.* 34:1577–1583 (1990)); TEM genes: C [5'-(TCGGGGAAATGTGCGCG)-3' (SEQ ID NO:5) and D [5'-(TGCTTAATCAGTGAGGCACC)-3' (SEQ ID NO:1) corresponding to nucleotide numbers 90 to 105 and 1062 to 1042, respectively, of Sutcliff et al., *Proc. Nat. Aca. Sci. USA*, 75:3737–3741 (1978). Primers A and B amplified a 885 base pair fragment while primers C and D amplified a 971 base pair fragment. The specificity of the SHV and TEM primers for amplification of SHV and TEM genes respectively was tested by using the following beta-lactamase controls; TEM-I (pACYC177), MIR-1 (from *K. pneumoniae*96D) and SHV-7 (pCLL3410).

PCR amplifications were carried out on a DNA Thermal Cycler 480 instrument (Perkin-Elmer, Cetus, Norwalk, Conn.) using the Gene Amp DNA amplification kit containing AmpliTaq polymerase (Perkin Elmer, Roche Molecular Systems, Inc., Branchburg, N.J.). The composition of the reaction mixture was as follows: 10 mM Tris-HCl (pH 8.3), 50 mM KCl, 0.1% TRITON X-100, 1.5 mM $MgCl_2$, 0.2 mM (each) of the four deoxynucleoside triphosphates, and 1.2 U of AmpliTaq in a total volume of 49 μl. A total of 1 μl of sample lysate was added to the reaction mixture, and was centrifuged briefly before 50 JA of mineral oil was layered on the surface. The PCR program consisted of an initial denaturation step at 96° C. for 15 seconds; followed by 24 cycles of DNA denaturation at 96° C. for 15 seconds, primer annealing at 50° C. for 15 seconds and primer extension at 72° C. for 2 minutes. After the last cycle the products were stored at 4° C. The PCR products (1/10 volume) were analyzed by electrophoresis using 1.4% agarose gels in TAE buffer (0.04 M Tris-acetate, 0.002 M EDTA [pH 8.5]). The gels were stained with ethidium bromide and the PCR products were visualized with ultra-violet light. A single band was observed for TEM amplified products using a single primer set. Two amplified products were observed with the SHV primer set. The larger product which corresponded to the expected size of the SHV specific product was gel purified using a 1.4% agarose in TAE gel and the purified PCR product was used for sequence analysis.

PCR products were sequenced by automated PCR cycle-sequencing with dye-terminator chemistry using a DNA stretch sequencer from Applied Biosystems.

Results

Resistance Phenotypes

All the strains except K. pneumoniae Pit 68, gave a positive disk potentiation when using cefotaxime, ceftriaxone, aztreonam and/or ceftazidime disks. Minimum inhibitory concentrations of piperacillin, piperacillin/tazobactam, cefotaxime, ceftazidime, aztreonam and cefoxitin revealed 3 different resistance phenotypes (Kpn1, 2 and 3) in the K. pneumoniae strains, and 2 (Ec1 and 2) in E. coli strains (Table 4).

The phenotypes Kpn1 and Ecd involved high level resistance to ceftazidime (MIC>128 μg/ml) but susceptibility to cefotaxime (MIC range 0.25–1 μg/ml), while Kpn2 and Ec2 involved decreased susceptibility to both cefotaxime (MIC range 4–64 μg/ml) and ceftazidime (MIC range 4–128 μg/ml). Kpn 3, represented by K. pneumoniae Pit 68, involved resistance to cefoxitin (MIC>128 μg/ml) and decreased susceptibility to cefotaxime, ceftazidime and aztreonam (MIC>2 μg/ml) (Table 4). The P. mirabilis isolates showed decreased susceptibility to ceftazidime (MIC range 16–64 μg/ml) and susceptibility to cefotaxime (MIC range 0.25–0.5 μg/ml).

Beta-Lactamases

Strains representing the Kpn1 and Ec1 phenotypes produced beta-lactamases with pI values of 5.6 and 7.6 respectively, while phenotypes Kpn2 and Ec2 involved enzymes with pI's of 5.4, 7.6, and 8.2 Cable 5). K. pneumoniae Pit 68, representing phenotype Kpn3, produced two beta-lactamases with pIs of 5.4 and 8.0. The P. mirabilis strains showed a single enzyme with a pI value of 5.6 (Table 5). The enzymes of pI 5.4, 5.6, 7.6 and 8.2 aligned with TEM-1 (pI 5.4), TEM-10 or 26 (pI 5.57), SHV-1, 2 or 8 (pI 7.6) and SHV-5 (pI 8.2) respectively (Table 5). It was therefore necessary to investigate these enzymes further. On isoelectric focusing gels, all of the beta-lactamases except for the enzymes with a pI of 8.0 were inhibited by clavulanate, a characteristic of Bush group 2 enzymes. The enzyme with a pI of 8.0 was inhibited by cloxacillin which correlates with Bush group 1 cephalosporinases. The substrate-based technique showed hydrolysis of 0.75 Fg/ml cefotaxime at the bands focusing at: 5.6, 8.0, 8.2 and some enzymes with a pI of 7.6 (Table 5). Control enzymes of TEM-10, TEM-26, SHV-2 and SHV-5 showed hydrolysis of cefotaxime in this assay (Table 5).

TABLE 4

Minimum Inhibitory Concentrations of the Different Resistance Phenotypes Observed in K. pneumoniae, E. coli and P. mirabilis.

| Resistance phenotype | No. strains | MIC range (μg/ml)[a] | | | | | | | |
|---|---|---|---|---|---|---|---|---|---|
| | | pip | tzp | ctx | caz | atm | fox | fep | imi |
| K. pneumoniae | | | | | | | | | |
| Kpn1 | 8 | >128 | 2–4 | 0.25–1 | >128 | 16–64 | 2–4 | 0.12 | 0.12 |
| Kpn2 | 28 | >128 | 2–>128 | 4–64 | 4–128 | 1–128 | 2–8 | 0.5–4 | 0.12–1 |
| Kpn3 | 1 | 64 | 16 | 4 | 4 | 2 | >128 | 0.12 | 0.12 |
| E. coli | | | | | | | | | |
| Ec1 | 3 | >128 | 1 | 1 | >128 | 16 | 4 | 0.12 | 0.12 |
| Ec2 | 1 | >128 | 32 | 16 | 4 | 2 | 8 | 2 | 0.12 |
| P. mirabilis | 4 | 128 | 0.25–0.5 | 0.25–0.5 | 16–64 | 0.5–2 | 2–4 | 2 | 0.5–1 |

[a]pip—piperacillin, tzp—piperacillin/tazobactam (4 μg/ml), ctx—cefotaxime, caz—ceftazidime, atm—aztreonam, fox—cefoxitin, fep—cefepime, imi—imipenem.

TABLE 5

Characteristics of Beta-lactamases Produced by Different Resistance Phenotypes.

| Resistance phenotype | No. strains | pI | ctx hydrolysis[a] | Inhibited[b] by; clox | clav | Most similar Beta-lactamases |
|---|---|---|---|---|---|---|
| *K. pneumoniae* | | | | | | |
| Kpn1 | 8 | 5.6 | Yes | No | Yes | TEM-10 or 26 |
| | | 7.6 | No | No | Yes | SHV-1 |
| Kpn2 | 28 | 5.4 | No | No | Yes | TEM-1 |
| | | 7.6 | Yes | No | Yes | SHV-2 or 8 |
| | | 8.2 | Yes | Yes | No | SHV-5 |
| Kpn3 | 1 | 5.4 | No | No | Yes | TEM-1 |
| | | 8.0 | Yes | Yes | No | AmpC |
| *E. coli* | | | | | | |
| Ec1 | 3 | 5.4 | No | No | Yes | TEM-1 |
| | | 5.6 | Yes | No | Yes | TEM-10 or 26 |
| Ec2 | 1 | 5.4 | No | No | Yes | TEM-1 |
| | | 7.6 | Yes | No | Yes | SHV-2 or 8 |
| *P. mirabilis* | 4 | 5.6 | Yes | No | Yes | TEM-10 or 26 |

[a]Hydrolysis of 0.75 μg/ml cefotaxime (ctx) used in substrate-based isoelectric focusing overlay technique (Hibbert-Rodgers et al., J. Antimicrob. Chemother., 33:707–720 (1994)).
[b]Inhibitors used in isoelectric focusing overlay technique were clav, clavulanic acid; clox, cloxacillin (Huletsky et al., Antimicrob. Agents and Chemother., 34:1725–1732 (1990)).

Hydrolysis assays with nitrocefin, cefotaxime, ceftazidime and aztreonam were performed on strains possessing single beta-lactamases. All the strains assayed hydrolyzed cefotaxime, ceftazidime and aztreonam to some extent (Table 6).

TABLE 6

Hydrolysis Profiles of Cell Extracts Containing a Single Beta-lactamase.
Hydrolysis (nmol of substrate[a] hydrolyzed/min/mg of protein)

| Strain | Beta-lactamase (pI) | Nitrocefin | Cefotaxime | Ceftazidime | Aztreonam |
|---|---|---|---|---|---|
| *K. pneumoniae* | | | | | |
| Pit 16 | 5.6 | 114 | 4 | 3 | 0.6 |
| Pit 100 | 7.6 | 159 | 11 | 0.1 | 0.9 |
| Pit 82 | 8.2 | 136 | 11 | 0.2 | 0.9 |
| *E. coli* | | | | | |
| Pit 64 | 5.6 | 275 | 1 | 2 | 0.4 |
| Pit 56 | 7.6 | 143 | 9 | 0.1 | 0.8 |
| *P. mirabilis* | | | | | |
| Pit 85 | 5.6 | 138 | 5 | 1 | 0.5 |

[a]100 μM solution of substrate

DNA Amplification and Sequencing

The DNA from organisms producing single beta-lactamases were amplified and sequenced. Strains producing ESBLs with pIs of 5.6, which aligned with TEM-10 and TEM-26, were amplified with the TEM primers (Table 7). Amino acids at positions 104, 164 and 240 (Ambler numbering (1)) were utilized to determine that this enzyme was more similar to TEM-26. Amino acids deduced from amplicon sequences included lysine at position 104, serine at position 164 and glutamine at position 240 Cable 7). Strains producing ESBLs with pI values 7.6 and 8.2, which aligned with SHV-2 and SHV-5 respectively, were amplified with SHV primers Cable 7). Amino acids at positions 205, 238 and 240 (Labia numbering (2)) were used to identify the ESBL involved. Arginine at position 205, serine at position 238 and glutamic acid at position 240 of the deduced amino acid sequence of strains producing an ESBL with a pI of 7.6 indicated the presence of SHV-2 (Table 7). *K. pneumoniae* Pit 82, producing an ESBL with a pI 8.2, had a lysine at position 240 indicating the presence of SHV-5 (Table 7).

TABLE 7

Identification of Extended-Spectrum Beta-lactamases Occurring in South Africa.

| Strain[a] | pI | Amplification with TEM primers | Amplification with SHV primers | TEM[b] aa 104 | TEM[b] aa 164 | TEM[b] aa 240 | SHV[c] aa 205 | SHV[c] Aa 238 | SHV[c] aa 240 | beta-lactamase |
|---|---|---|---|---|---|---|---|---|---|---|
| *K. pneumoniae* | | | | | | | | | | |
| Pit 16 | 5.6 | Yes | No | Lys | Ser | Glu | — | — | — | TEM-26-type |
| Pit 100 | 7.6 | No | Yes | — | — | — | Arg | Ser | Glu | SHV-2 |
| Pit 82 | 8.2 | No | Yes | — | — | — | Arg | Ser | Lys | SHV-5 |
| *E. coli* | | | | | | | | | | |
| Pit 64 | 5.6 | Yes | No | Lys | Ser | Glu | — | — | — | TEM-26-type |
| Pit 56 | 7.6 | No | Yes | — | — | — | Arg | Ser | Glu | SHV-2 |
| *P. mirabilis* | | | | | | | | | | |
| Pit 85 | 5.6 | Yes | No | Lys | Ser | Glu | — | — | — | TEM-26-type |

[a]Strains with single beta-lactamases used for sequencing
[b]Numbering according to Sutcliffe et al., Proc. Nat. Aca. Sci., USA, 75, 3737–3741 (1978).
[c]Numbering according to Mercier et al., Antimicrob. Agents Chemother., 34, 1577–1583 (1990).

EXAMPLE 3

Plasmid-Mediated Resistance to Expanded-Spectrum Cephalosporins among *Enterobacter aerogenes*

Materials and Methods

Bacterial Strains

Among all *E. aerogenes* recovered from clinical specimens during an eighteen month period (September 1993 to March 1995), thirty-one *E. aerogenes* strains showing a resistance phenotype different from that observed with derepressed mutants normally encountered at the Hunter Holmes McGuire Medical Center, Richmond, Va. were selected for this study. The strains selected were intermediate to ceftriaxone but resistant to ceftazidime when tested with the Vitek automated susceptibility system (bioMerieux Vitek, St. Louis, Mo.). Derepressed mutants previously isolated from this center were usually resistant to both ceftriaxone and ceftazidime.

Susceptibility Testing

Antibiotic susceptibilities were determined by standard disk-diffusion (NCCLS Standard M2-A6) and agar-dilution (NCCLS Standard M7-A4) procedures. Disks were obtained from Becton Dickinson Microbiology Systems (Cockeysville, Md.). Disk-diffusion susceptibilities to the following antibiotics were determined, ampicillin; amoxicillin clavulanic acid; aztreonam; cefazolin; cefoxitin; cefuroxime; cefotaxime; ceftriaxone; ceftazidime; cefepime; imipenem; gentamicin; trimethoprim/sulfamethoxazole and ciprofloxacin. Standard powders of antimicrobial agents for minimum inhibitory concentration (MICS) were kindly provided by the following companies: cefoxitin and imipenem, (Merck, Rathway N.J.); cefotaxime, (Hoechst-Roussel Pharmaceuticals Inc., Somerville, N.J.); ceftazidime, (Glaxo Group Research Ltd., Greenford England); aztreonam and cefepime, (Bristol-Myers Squibb, Princetown, N.J.) and gentamicin, (Schering-Plough, Liberty Corner, N.J.). The following quality control strains were run simultaneously with the test organisms *Escherichia coli* ATCC 25922, *Pseudomonas aeruginosa* ATCC 27853, and *E. coli* ATCC 35218. Throughout this study, results were interpreted using NCCLS criteria for disk diffusion (NCCLS M2-A6) and broth dilution (NCCLS M7-A4).

Double-Disk Potentiation Test

This test described by Jarlier et al., Rev. Infect. Dis. 10:867–878 (1988), using ceftazidime, ceftriaxone, cefotaxime and aztreonam disks was performed on the strains to screen for possible ESBL production. This test is a modification of the disk diffusion susceptibility test in that cefotaxime, ceftriaxone, ceftazidime and aztreonam disks are placed 30 mm from disks containing amoxycillin/clavulanic acid. A potentiation of the zones of cefotaxime, ceftriaxone, ceftazidime or aztreonam by clavulanic acid represented a positive test and was indicative of possible ESBL production.

Beta-lactamase Preparation. Isoelectric Focusing and Assays

Overnight cultures in 5 mls Mueller-Hinton broth were diluted with 95 ml fresh broth and incubated with shaking for 90 minutes at 37° C. Cefoxitin, at a concentration of ¼ of the MIC, was added for induction while sterile medium was used in the non-induced cultures and incubated for an additional 2 hours. The induction process was stopped by adding 1 mM 8-hydroxyquinoline solution to each culture. Cells were harvested by centrifugation at 4° C., washed with 1M potassium-phosphate buffer (pH 7.0), suspended and sonicated. After sonication, crude extracts were obtained by centrifugation at 6,000 rpm for 1 hour. The beta-lactamases in the sonic extracts were assessed for isoelectric points (pIs), and substrate and inhibitor profiles in polyacrylamide gels. The rates of hydrolysis of cephalothin were determined by ultra-violet spectrophotometric assay (O'Callghan et al., Antimicrob. Agents and Chemother., 1966, 337–343 (1967)). As controls, crude beta-lactamase preparations from the following organisms possessing different SHV enzymes were evaluated simultaneously with those obtained from the *Enterobacter* strains: SHV-1 [from *E. coli* J53(R1010)], SHV-2 (from *Klebsiella ozaenae* 2180), SHV-3 [from *E. coli* J53-2(pUD18)], SHV-4 [from *E. coli* J53-2(pUD21)] and SHV-5 [from *E. coli* Cla Nal (pAFF2)].

Isolation of Plasmids

The organisms were inoculated into 5 ml of LB (Luria Bertani) broth [Difco (Detroit, Mich.)] and incubated for 20 hours at 37° C. with shaking. Cells from 1.5 ml of overnight culture were harvested by centrifugation in an Eppendorf centrifuge for 5 minutes. After the supernatant was decanted, the pellet was resuspended in TRITON X100 1% in TE buffer for 10 minutes. Plasmid DNA was then isolated by the alkaline extraction method of Birnboim et al., *Nucleic Acids Res.*, 7:1513 (1979), and separated by electrophoresis in 0.8% agarose gel (Sigma, St. Louis, Mo.) in TAE buffer (0.04M Tris-acetate, 0.002M EDTA [pH 8.5]). The gel was stained with ethidium bromide and plasmid bands were visualized using ultra-violet light.

Conjugation Experiments

To determine if the resistance was transferable, transconjugation experiments were performed using *Escherichia coli* C600N(Nal$^r$) as recipient (Maniatis et al., *Molecular Cloning: A Laboratory Manual*, Cold Spring Harbor, N.Y., 1982). The filter paper mating technique with overnight incubation at 37° C. were performed as described previously (Philippon et al., *Antimicrob. Agents Chemother.*, 33:1131–1136 (1989)). Transconjugants were selected on LB (Luria Bertani) agar [Difco (Detroit, Mich.)] plates containing 12 µg per ml nalidixic acid and 20 µg per ml ampicillin.

DNA Amplification Using the Polymerase Chain Reaction (PCR)

Organisms were inoculated into 5 ml of LB (Luria Bertani) broth [Difco (Detroit, Mich.)] and incubated for 20 hours at 37° C. with shaking. Cells from 1.5 ml of overnight culture were harvested by centrifugation at 13,000 rpm in an Eppendorf centrifuge for 5 minutes. After the supernatant was decanted, the pellet was resuspended in 500 µl of sterile deionized water. The cells were lysed by heating to 95° C. for 10 minutes and cellular debris were removed by centrifugation for 5 minutes at 13,000 rpm. The supernatant was used as a source of template for amplification. Oligonucleotide primers specific for SHV genes were selected from a consensus alignment sequence generated by the MacVector 4.5 (Kodak/IBI) software package from the published nucleic acid sequence of SHV-1 (Mercier et al., *Antimicrob. Agents Chemother.*, 34:1577–1583 (1990)), SHV-2 (Jacoby et al., *Antimicrob. Agents Chemother.* 35:1697–1704 (1991)), SHV-5 (Billot-Klein et al., *Antimicrob. Agents Chemother.*, 34:2439–2441 (1990)) and SHV-7 (Bradford et al., *Antimicrob. Agents Chemother.*, 39:899–905 (1995)). The PCR primers used were A [5'-(CACTCAAGGATGTATTGTG)-3'] (SEQ ID NO:10) and B [5'-(TTAGCGTTGCCAGTGCTCG)-3'] (SEQ ID NO:11) which amplified a 781 base pair fragment. Primer specificity controls included the TEM-1, MIR-1 and SHV-7 beta-lactamase genes. PCR amplifications were carried out on a DNA Thermal Cycler 480 instrument (Perkin-Elmer, Cetus, Norwalk, Conn.) using the GeneAmpDNA amplification kit containing AmpliTaqpolymerase (Perkin Elmer, Roche Molecular Systems, Inc., Branchburg, N.J.). The composition of the reaction mixture was as follows: 10 mM Tris-HCl (pH 8.3), 50 mM KCl, 0.1% TRITON X-100, 1.5 mM MgCl$_2$, 0.2 mM (each) of the four deoxynucleoside triphosphates, and 1.2 U of AmpliTaqin a total volume of 49 µl. A total of 1 µl of sample lysate was added to the reaction mixture, and was centrifuged briefly before 50 µl of mineral oil was layered on the surface. The PCR program consisted of an initial denaturation step at 96° C. for 30 seconds; followed by 24 cycles of DNA denaturation at 96° C. for 30 seconds, primer annealing at 50° C. for 15 seconds and primer extension at 72° C. for 2 minutes. After the last cycle the products were stored at 4° C. The PCR products were analyzed by electrophoresis using 1.4% agarose gels in TAE buffer. The gels were stained with ethidium bromide and the PCR products were visualized with ultra-Ill violet light.

Results

Bacterial Strains

Twenty-four of the 31 strains from Hunter Holmes McGuire Medical Center originated from patients in 2 spinal cord injury wards (SCW1, SCW2) while 3 strains were isolated from patients in the medical intensive care unit, 3 isolates were recovered from patients attending the surgical outpatient clinic, and 1 isolate was recovered from a patient in a general surgery ward. Disk diffusion susceptibility tests showed all the strains to be resistant to ampicillin, amoxycillin-clavulanate, cefazolin, cefuroxime, trimethoprim/sulfamethoxazole and susceptible to ciprofloxacin. MICs for cefoxitin, cefotaxime, ceftazidime, aztreonam, cefepime, imipenem and gentamicin are summarized in Table 8, below. All strains were susceptible to cefepime and imipenem but showed decreased susceptibility to cefotaxime, ceftazidime and aztreonam. MICs for gentamicin ranged from 8 µg/ml to >128 µg/ml for 25 of 37 (67%) isolates. All the strains selected for this study showed a positive double disk test when using cefotaxime and ceftriaxone disks.

TABLE 8

Minimum Inhibitory Concentrations and Characteristics of Beta-lactamases Produced by *E. aerogenes.*

| | | Enzyme Characteristics | | | | | MIC (µg/ml)range[a] | | | | | | |
|---|---|---|---|---|---|---|---|---|---|---|---|---|---|
| No. of Strains | Beta-lactamase[b] Present | pI | Hydrolysis[c] | Inhibited by[d]: clox | clav | Inducible[e] | fox | ctx | caz | atm | fep | imi | gm |
| 1 | Bush group 1 | 8.3 | no | yes | no | yes | >256 | 1 | 4 | 1 | 0.12 | 0.5 | 8 |
| | Bush group 2be (SHV-3) | 6.9 | yes | no | yes | no | | | | | | | |
| 29 | Bush group 1 | 8.3 | no | yes | no | yes | >256 | 1–2 | 8–32 | 32–64 | 0.12–1 | 0.5 | 1–16 |
| | Bush group 2be (SHV-4) | 7.8 | yes | no | yes | no | | | | | | | |

TABLE 8-continued

Minimum Inhibitory Concentrations and Characteristics of Beta-lactamases Produced by *E. aerogenes*.

| | | Enzyme Characteristics | | | | | | | | | | | |
|---|---|---|---|---|---|---|---|---|---|---|---|---|---|
| No. of | Beta-lactamase[b] | | Ctx | Inhibited by[d]: | | | MIC (μg/ml)range[a] | | | | | | |
| Strains | Present | pI | Hydrolysis[c] | clox | clav | Inducible[e] | fox | ctx | caz | atm | fep | imi | gm |
| 1 | Bush group 1 | 8.3 | no | yes | no | yes | >256 | 1–2 | 32 | 64 | 1 | 1 | >128 |
| | Bush group 2Be (SHV-5) | 8.0 | yes | no | yes | no | | | | | | | |

[a]Cefoxitin (fox); cefotaxime (ctx); ceftazidime (caz); aztreonam (atm); cefepime (fep); imipenem (imi); gentamicin (gm).
[b]Based on Bush-Jacoby-Medeiros classification (Antimicrob. Agents Chemother., 39:899–905 (1995)). Beta-lactamase listed in parentheses is the one most similar to the group 2be enzyme produced by the *Enterobacter* strains.
[c]Hydrolysis of 0.75 μg/ml cefotaxime (ctx) used in substrate-based isoelectric focusing overlay technique (Bauernfeind et al., Infection 18:294–298 (1990)).
[d]Inhibitors used in isoelectric focusing overlay technique were clav, clavulanic acid; clox, cloxacillin (Sanders et al., Clin. Microbiol. Rev., 10:220–241 (1997)).
[e]Inducible by cefoxitin.

Characteristics of Beta-lactamases.

All the *Enterobacter* isolates possessed a Bush group 1 inducible beta-lactamase with an alkaline pI of 8.3 which was sensitive to inhibition by cloxacillin but not clavulanic acid (Table 8, above). Additional Bush group 2be enzymes with pIs resembling SHV beta-lactamases were also present in all the strains (Table 8). Three different Bush group 2be enzymes were detected in the species of *Enterobacter* (Table 8): the majority of isolates (29 of 31) produced an enzyme with a pi of 7.8 which aligned with SHV-4. One isolate produced an enzyme with a pi of 6.8 which aligned with SHV-3, and one isolate produced an enzyme with a pi of 8.2 which aligned with SHV-5.

Plasmid Profiles

A variety of different plasmids with sizes ranging from 10 kb to approximately 60 kb were visualized with electrophoresis (Table 9, below). Furthermore, eight different plasmid patterns were observed with the number of plasmids ranging from 0 to 5 per organism (Table 9). No plasmids were visualized in 3 strains, which included the strain which produced an enzyme resembling SHV-5 (Table 9). Three different susceptibility profiles were identified (Table 9). The majority of organisms isolated were resistant to ceftazidime, aztreonam, trimethoprim/sulfamethoxazole and gentamicin. This antibiogram was associated with the production of β-lactamases resembling SHV-4 and SHV-5 and were isolated from the spinal cord injury wards 1 and 2, medical intensive care unit, general surgical ward as well as the outpatient clinic (Table 9). Eight of thirty strains showing 3 different plasmid profiles (a, b and f) producing an enzyme resembling SHV-4 isolated from SCW1 as well as the surgical outpatient clinic were susceptible to gentamicin while the *E. aerogenes* strain producing an enzyme resembling SHV-3 appeared susceptible to ceftazidime and aztreonam (Table 9). Seven different plasmid profiles (b–h) were observed among *E. aerogenes* isolated from the spinal cord injury ward SCW1 while only 4 patterns (c, d, g and h) were observed among those recovered from SCW2 Cable 9). Plasmid profile b, observed in 6 isolates, consisting of 5 plasmids ranging from 50 kb to 10 kb and plasmid profile f, observed in 1 isolate (3 plasmids ranging from 60 kb to 10 kb) were unique to SCW1 Cable 9). Two of the three strains isolated from MICU possessed 4 plasmids ranging from 60 kb to 10 kb (plasmid profile c) while no plasmids were visualized from the other strain (plasmid profile h) [Table 9]. These organisms produced an enzyme resembling SHV-4 and were resistant to ceftazidime, aztreonam, trimethoprim/sulfamethoxazole and gentamicin. The *E. aerogenes* strains originating from the surgical outpatient clinic had 2 different antibiograms and plasmid profiles. Two of three isolates, possessing plasmid profile e, were resistant to ceftazidime, aztreonam, trimethoprim/sulfamethoxazole and gentamicin while the remaining isolate with plasmid profile a, appeared susceptible to gentamicin (sable 9). All these organisms produced an enzyme resembling SHV-4.

TABLE 9

Plasmid Profiles of *Enterobacter aerogenes*.

| Plasmid profile | No. plasmids | Approximate Size (kilobases) | Ward (no. of isolates)[a] | Antibiogram[b] | Most Likely ESBL |
|---|---|---|---|---|---|
| A | 5 | 50, 35, 20, 15, 12 | OPC(1) | CAZ/ATM/SXT | SHV-4 |
| B | 5 | 50, 45, 35, 20, 10 | SCW1(6) | CAZ/ATM/SXT | SHV-4 |
| C | 4 | 60, 45, 20, 10 | SCW1(5) | CAZ/ATM/SXT/G | SHV-4 |
| | | | SCW2(2) | CAZ/ATM/SXT/G | SHV-4 |
| | | | MICU(2) | CAZ/ATM/SXT/G | SHV-4 |
| D | 4 | 45, 35, 20, 10 | SCW1(2) | CAZ/ATM/SXT/G | SHV-4 |
| | | | SCW2(1) | CAZ/ATM/SXT/G | SHV-4 |
| E | 3 | 60, 50, 14 | SCW1(2) | CAZ/ATM/SXT/G | SHV-4 |
| | | | OPC(2) | CAZ/ATM/SXT/G | SHV-4 |

TABLE 9-continued

Plasmid Profiles of *Enterobacter aerogenes.*

| Plasmid profile | No. plasmids | Approximate Size (kilobases) | Ward (no. of isolates)[a] | Antibiogram[b] | Most Likely ESBL |
|---|---|---|---|---|---|
| F | 3 | 60, 50, 10 | SCW1(1) | CAZ/ATM/SXT | SHV-4 |
| G | 2 | 50, 10 | SCW1(1) | SXT/G | SHV-3 |
|   |   |   | SCW2(2) | CAZ/ATM/SXT/G | SHV-4 |
|   |   |   | SGW(1) | CAZ/ATM/SXT/G | SHV-4 |
| H | 0 | — | SCW1(1) | CAZ/ATM/SXT/G | SHV-5 |
|   |   |   | SCW2(1) | CAZ/ATM/SXT/G | SHV-4 |
|   |   |   | MICU(1) | CAZ/ATM/SXT/G | SHV-4 |

[a]OPC; outpatient clinic, SCW1; spinal cord injury ward 1, SCW2; spinal cord injury ward 2, MICU; medical intensive care unit, SGW; surgical general ward.
[b]Resistance to CAZ; ceftazidime, ATM; aztreonam, SXT; trimethoprim/sulfamethoxazole, G; gentamicin.

Conjugation Experiments

The following strains were selected for conjugation with *E. coli* C600N. *E. aerogenes* 187 producing an enzyme with a pI of 6.8 resembling SHV-3; *E. aerogenes* 200 and *E. aerogenes* 220 producing enzymes with pIs of 7.8 resembling SHV-4; and *E. aerogenes* 184 producing an enzyme with a pI of 8.2 resembling SHV-5. All the strains also possessed an inducible Bush group 1 beta-lactamase with a pI of 8.3. A plasmid of approximately 50 kb was transferred from *E. aerogenes* 187, *E. aerogenes* 200 and *E. aerogenes* 220 to *E. coli* C600N (Table 10, below). No plasmids were visualized in *E. aerogenes* 184 or its transconjugant *E. coli* JP04/tr (Table 10). Isoelectric focusing performed on the *Enterobacter* strains and their respective transconjugants showed the beta-lactamases resembling SHV-3, SHV-4 and SHV-5 present in both donors and recipients. The transfer of plasmids encoding SHV beta-lactamase genes into *E. coli* C600N was accompanied by resistance to gentamicin and trimethroprim/sulfamethoxazole and decreased susceptibility to cefotaxime, ceftazidime and aztreonam (Table 10).

TABLE 10

Characteristics of *Enterobacter* Strains and Respective Transconjugants

| Strains[a] | Plasmids (approximate size, kilobases) | Beta-lactamases (pI) | Most likely Beta-lactamase |
|---|---|---|---|
| *E. coli* C600N | — | — | — |
| *E. aerogenes* 187 | 50, 10 | 8.3, 6.8 | AmpC, SHV-3 |
| *E. coli* JP01/tr | 50 | 6.8 | SHV-3 |
| *E. aerogenes* 200 | 60, 50, 14 | 8.3, 7.8 | AmpC, SHV-4 |
| *E. coli* JP02/tr | 50, 10 | 7.8 | SHV-4 |
| *E. aerogenes* 220 | 60, 50, 10 | 8.3, 7.8 | AmpC, SHV-4 |
| *E. coli* JP03/tr | 50 | 7.8 | SHV-4 |
| *E. aerogenes* 184 | — | 8.3, 8.2 | AmpC, SHV-5 |
| *E. coli* JP04/tr | — | 8.2 | SHV-5 |

[a]*E. aerogenes* 187, 200, 220 and 184 were donors; *E. coli* C600N served as recipient and JP01, 2, 3 and 4 were the respective transconjugants DNA Amplification The strains used in the conjugation experiments were selected for amplification with PCR; *E. aerogenes* 187 (pI 6.8), *E. aerogenes* 200 (pI 7.8), *E. aerogenes* 220 (pI 7.8), *E. aerogenes* 184 (pI of 8.2) as well as their respective transconjugants *E. coli* JP01/tr (pI 6.8), *E. coli* JP02/tr (pI 7.8), *E. coli* JP03/tr (pI 7.8) JP04/tr (pI 8.2). Control strains producing SHV-3, SHV-4, SHV-5 and SHV-7 were used as positive controls while *E. coli* C600N was used as a negative control. A 781 base pair fragment specific for SHV beta-lactamases was amplified in *E. aerogenes* 187, *E. aerogenes* 200, *E. aerogenes* 220, *E. aerogenes* 184 and their respective transconjugants as well as the positive controls (Table 10, above). No amplification was observed with *E. coli* C600N (Table 10). Therefore, the ESBLs produced by these strains are indeed derivatives of an SHV beta-lactamase.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

Sequence Listing Free Text

SEQ ID NO:1–45 Primer

What is claimed is:

1. A primer selected from the group of:
5'-CTC GAT GAT GCG TGC TTC GC-3' (SEQ ID NO:32);
5'-GCG ACT GTG ATG TAT AAA CG-3' (SEQ ID NO:33); ad full-length compliments thereof.

2. A method for identifying a PSE1, PSE4, or CARB3 family beta-lactamase within Gram Negative bacteria in a clinical sample, the method comprising:
providing a pair of oligonucleotide primers, each having 15–35 nucleotides, specific for nucleic acid characteristic of the PSE1, PSE4, and CARB3 beta-lactamase enzymes, wherein one primer of the pair is complementary to at least a portion of the beta-lactamase nucleic acid in the sense strand and the other prier of each pair is complementary to at least a portion of the beta-lactamase nucleic acid in the antisense strand;
annealing the primers to the beta-lactamase nucleic acid;
simultaneously extending the annealed primers from a 3' terminus of each primer to synthesize an extension product that is complementary to the nucleic acid strands annealed to each primer wherein each extension product after separation from the beta-lactamase nucleic acid serves as a template for the synthesis of an extension product using a primer that is complementary to said each extension product;
separating the amplified products; and
analyzing the separated amplified products for a region characteristic of the beta-lactamase: wherein the priers are selected from the group of;
5'-CTC GAT GAT GCG TGC TTC GC-3' (SEQ ID NO:32):
5'-GCG ACT GTG ATG TAT AAA CG-3' (SEQ ID NO:33)-, and full-length complements thereof.

3. A diagnostic kit for detecting a PSE1, PSE4, or CARB3 family beta-lactamase within Gram Negative bacteria which comprises packaging, containing, separately packaged:
(a) at least one primer pair capable of hybridizing to a beta-lactamase nucleic acid characteristic of the PSE1, PSE4, and CARB3 families of beta-lactamase enzymes, wherein each primer of the pair includes 15–35 nucleotides;
(b) a positive and negative control; and
(c) a protocol for identification of the beta-lactamase nucleic acid characteristic of the PSE1, PSE4, or CARB3 families of beta-lactamase enzymes;
wherein at least one of the primers is selected from the group consisting of:
5'-CTC GAT OAT GCG TGC TTC OC-3' (SEQ ID NO:32);
5'-GCG ACT ATG ATO TAT AAA CG-3' (SEQ ID NO:33); and full-length complements thereof.

* * * * *

UNITED STATES PATENT AND TRADEMARK OFFICE
CERTIFICATE OF CORRECTION

PATENT NO. : 6,893,846 B2
DATED : May 17, 2005
INVENTOR(S) : Nancy D. Hanson et al.

It is certified that error appears in the above-identified patent and that said Letters Patent is hereby corrected as shown below:

Column 4,
Line 5, delete "*Science*, 2" and insert -- *Science*, 230 --.

Column 29,
Lines 31, 32 and 33, delete "pi" and insert -- pI --.

Column 30,
Line 50, delete "(sable)" and insert -- (Table) --.

Column 47,
Line 7, delete "ad" and insert -- and --.
Line 16, delete "prier" and insert -- primer --.

Column 48,
Line 2, delete "priers" and insert -- primers --.
Line 23, delete "OAT" and insert -- GAT --.
Line 23, delete "OC" and insert -- GC --.
Line 25, delete "ATG ATO" and insert -- GTG ATG --.

Signed and Sealed this

Twenty-eighth Day of February, 2006

JON W. DUDAS
*Director of the United States Patent and Trademark Office*